(12) United States Patent
Tremblay et al.

(10) Patent No.: US 12,400,452 B2
(45) Date of Patent: Aug. 26, 2025

(54) NON-CONTACT TEMPERATURE MEASUREMENT IN THERMAL IMAGING SYSTEMS AND METHODS

(71) Applicant: Teledyne FLIR, LLC, Thousand Oaks, CA (US)

(72) Inventors: Louis Tremblay, Goleta, CA (US); Pierre M. Boulanger, Goleta, CA (US); Justin Muncaster, Goleta, CA (US); James Klingshirn, Goleta, CA (US); Robert Proebstel, Goleta, CA (US); Giovanni Lepore, Peabody, MA (US); Eugene Pochapsky, Freeport, PA (US); Katrin Strandemar, Rimbo (SE); Nicholas Högasten, Santa Barbara, CA (US); Karl Rydqvist, Täby (SE); Theodore R Hoelter, Santa Barbara, CA (US); Jeremy P. Walker, Oakmont, PA (US); Per O. Elmfors, Goleta, CA (US); Austin A. Richards, Santa Barbara, CA (US); Dylan M. Rodriguez, Goleta, CA (US); John C. Day, Goleta, CA (US); Hugo Hedberg, Täby (SE); Tien Nguyen, Wilsonville, OR (US); Fredrik Gihl, Täby (SE); Rasmus Loman, Täby (SE)

(73) Assignee: Teledyne FLIR, LLC, Thousand Oaks, CA (US)

( * ) Notice: Subject to any disclaimer, the term of this patent is extended or adjusted under 35 U.S.C. 154(b) by 308 days.

(21) Appl. No.: 17/960,750

(22) Filed: Oct. 5, 2022

(65) Prior Publication Data
US 2023/0043342 A1 Feb. 9, 2023

Related U.S. Application Data

(63) Continuation of application No. PCT/US2021/026060, filed on Apr. 6, 2021.
(Continued)

(51) Int. Cl.
*G06V 20/52* (2022.01)
*A61B 5/00* (2006.01)
(Continued)

(52) U.S. Cl.
CPC .............. *G06V 20/52* (2022.01); *A61B 5/015* (2013.01); *A61B 5/7264* (2013.01); *A61B 5/746* (2013.01);
(Continued)

(58) Field of Classification Search
None
See application file for complete search history.

(56) References Cited

U.S. PATENT DOCUMENTS 7,340,293 B2   3/2008   McQuilkin
9,733,458 B2   8/2017   Georgiev et al.
(Continued)

FOREIGN PATENT DOCUMENTS

CN       110378234 A      10/2019
WO    WO 2015103446 A2    7/2015
(Continued)

OTHER PUBLICATIONS

Thomas et al., "Axillary and Thoracic Skin Temperatures Poorly Comparable to Core Body Temperature", Biol Res Nurs., Jan. 2004, pp. 187-194, 5(3), Sage Publications, California, United States of America, Abstract.
(Continued)

*Primary Examiner* — Edwin C Gunberg
(74) *Attorney, Agent, or Firm* — Haynes and Boone, LLP

(57) ABSTRACT

Systems and methods include an image capture component configured to capture infrared images of a scene, and a logic device configured to identify a target in the images, acquire temperature data associated with the target based on the images, evaluate the temperature data and determine a corresponding temperature classification, and process the identified target in accordance with the temperature classification. The logic device identifies a person and tracks the person across a subset of the images, identify a measurement location for the target in a subset of the images based on
(Continued)

target feature points identified by a neural network, and measure a temperature of the location using corresponding values from one or more captured thermal images. The logic device is further configured calculate a core body temperature of the target using the temperature data to determine whether the target has a fever and calibrate using one or more black bodies.

20 Claims, 28 Drawing Sheets

Related U.S. Application Data

(60) Provisional application No. 63/090,691, filed on Oct. 12, 2020, provisional application No. 63/006,063, filed on Apr. 6, 2020.

(51) Int. Cl.

| | |
|---|---|
| *A61B 5/01* | (2006.01) |
| *G01J 5/00* | (2022.01) |
| *G01J 5/70* | (2022.01) |
| *G06T 7/73* | (2017.01) |
| *G06V 10/25* | (2022.01) |
| *G06V 10/774* | (2022.01) |
| *G06V 10/82* | (2022.01) |
| *G06V 40/16* | (2022.01) |
| *G08B 21/18* | (2006.01) |
| *H04N 23/45* | (2023.01) |
| *H04N 23/69* | (2023.01) |
| *H04N 23/698* | (2023.01) |

(52) U.S. Cl.
CPC ............... *G01J 5/0025* (2013.01); *G01J 5/70* (2022.01); *G06T 7/73* (2017.01); *G06V 10/25* (2022.01); *G06V 10/774* (2022.01); *G06V 10/82* (2022.01); *G06V 40/168* (2022.01); *G08B 21/182* (2013.01); *H04N 23/45* (2023.01); *H04N 23/69* (2023.01); *H04N 23/698* (2023.01); *G01J 2005/0077* (2013.01); *G06T 2200/24* (2013.01); *G06T 2207/10048* (2013.01); *G06T 2207/20081* (2013.01); *G06T 2207/20084* (2013.01); *G06T 2207/30201* (2013.01); *G06V 2201/07* (2022.01)

(56) References Cited

U.S. PATENT DOCUMENTS

| | | | | |
|---|---|---|---|---|
| 2007/0153871 | A1* | 7/2007 | Fraden | A61B 5/015 374/121 |
| 2015/0213317 | A1 | 7/2015 | Chiang et al. | |
| 2016/0156880 | A1 | 6/2016 | Teich et al. | |
| 2016/0262631 | A1 | 9/2016 | Shen | |
| 2019/0192010 | A1* | 6/2019 | Mane | A61B 5/165 |
| 2019/0205655 | A1 | 7/2019 | Matsuoka et al. | |
| 2020/0146557 | A1* | 5/2020 | Cheung | H04N 23/90 |

FOREIGN PATENT DOCUMENTS

| | | |
|---|---|---|
| WO | WO 2016087622 A1 | 6/2016 |
| WO | WO 2016182962 A1 | 11/2016 |

OTHER PUBLICATIONS

Dixon et al., Thermal variations of the human eye., Transactions of the American Ophthalmological Society, 1991, pp. 183-190, vol. 89, PubMed, Maryland, United States of America.
Pascoe et al., "International standards for pandemic screening using infrared thermography", Medical Imaging 2010: Biomedical Applications in Molecular, Structural, and Functional Imaging, Mar. 9, 2010, 3 pages, Proceedings vol. 7626, San Diego, California, United States of America, Abstract.
Teunissen et al., "Infrared thermal imaging of the inner canthus of the eye as an estimator of body core temperature", Journal of Medical Engineering and Technology, Jan. 9, 2011, pp. 134-138, 35(3-4), Informa UK Limited, London, England.
Childs et al., "Infra-red thermal imaging of the inner canthus correlates with the temperature of the injured human brain", Engineering, Oct. 2012, pp. 53-56, vol. 4 No. 10B, SciRes, Wuhan, China.
Rossignoli et al., "Reliability of infrared thermography in skin temperature evaluation of wheelchair users", Spinal Cord, Nov. 25, 2014, pp. 243-248, vol. 53, International Spinal Cord Society, Aylesbury, United Kingdom.
Chiang et al., "Mass screening of suspected febrile patients with remote sensing infrared thermograhpy alarm temperature and optimal distance", Journal of the Formosan Medical Association, Dec. 2008, pp. 937-944, vol. 107, Issue 12, JFMA, Tapei, Taiwan.
Fenemore et al., "Validity of a Tympanic Thermometer and Thermal Imaging Camera for Measuring Core and Skin Temperature during Exercise in the Heat", Measurement in Physical Education and Exercise Science, Sep. 2019, pp. 49-55, vol. 24:1, Informa UK Limited, London, United Kingdom, Abstract.
Ghassemi et al., "Standardized assessment of infrared thermographic fever screening system performance", Design and Quality for Biomedical Technologies X, Mar. 14, 2017, 28 pages, Proc. SPIE vol. 10056, SPIE, San Francisco, California, United States of America.
Ghassemi et al., "Multi-modality image registration for effective thermographic fever screening", BiOS, Feb. 2017, 19 pages, Proc. SPIE 10057, SPIE, California, United States of America.
James et al., "Reliability and validity of skin temperature measurement by telemetry thermistors and a thermal camera during exercise in the heat", Journal of Thermal Biology, Sep. 3, 2014, pp. 141-149, vol. 45, Elsevier, Amsterdam, Netherlands.
Hildy et al., "Rectal and bladder temperatures vs forehead core temperatures measured with SpotOn monitoring system", American journal of critical care: an official publication, Jan. 27, 2018, pp. 43-50, vol. 27, 1, American Association of Critical-Care Nurses, Aliso Viejo, California, United States of America, Abstract.
Vardasca et al., "Bilateral assessment of body core temperature through axillar, tympanic and inner canthi thermometers in a young population", Physiological Measurement, Sep. 30, 2019, 9 pages, vol. 40, 9, IOP Publishing, Bristol, United Kingdom.
Vardasca et al., "The influence of angles and distance on assessing inner-canthi of the eye skin temperature", Thermology International, Nov. 2017, pp. 130-135, 27(4), European Association of Thermology, Vienna, Austria.
Chan et al., "Screening for Fever by Remote-sensing Infrared Thermographic Camera", Journal of Travel Medicine, Sep. 2004, pp. 273-279, 11(5), PubMed, Maryland, United States of America.
Liu et al., "Limitations of Forehead Infrared Body Temperature Detection for Fever Screening for Severe Acute Respiratory Syndrome", Infection Control and Hospital Epidemiology, Dec. 2004, pp. 1109-1111, vol. 25, 12, PubMed, Maryland, United States of America.
Dileo et al., "Effect of Wearing an N95 Filtering Facepiece Respirator On Superomedial Orbital Infrared Indirect Brain Temperature Measurements", Journal of Clinical Monitoring and Computing, Jan. 2016, pp. 67-73, vol. 31, 1, PubMed, Maryland, United States of America.
Kim et al., "The Correlation Between Tympanic Membrane Temperature and Specific Region of Face Temperature", Quantitative InfraRed Thermography Journal, Nov. 2018, pp. 1-7, vol. 16:1, Informa UK Limited, London, United Kingdom.
Barnard et al., "Effect of fever on menopausal hot flashes", Maturitas, Mar. 1992, pp. 181-189, vol. 14, 3, EMAS, Berlin, Germany, Abstract.
Hinnerichs, Christopher M., "Efficacy of Fixed Infrared Thermography for Identification of Subjects with Influenza-like Illness", Dissertation, Aug. 2011, 141 pages, Walden University, Minnesota, United States of America.

(56) References Cited

OTHER PUBLICATIONS

Ghassemi et al., "Free form deformation approach for registration of visible and infrared facial images in fever screening", Sensors, Jan. 2018, 14 pages, 18, 25, MDPI, Basel, Switzerland.

Ghassemi et al., "Best practices for standardized performance testing of infrared thermographs intended for fever screening", PLoS One, Sep. 2018, 24 pages, 13(9), PubMed, Maryland, United States of America.

Pascoe, David D., "Comparison of Measuring Sites for the Assessment of Body Temperature: Final Amendment", Letter to the Editor, Jan. 2010, pp. 36-38, vol. 20, 1, Thermography International, Vienna, Austria.

Fernandes et al., "Validity of inner canthus temperature recorded by infrared thermography as a non-invasive surrogate measure for core temperature at rest, during exercise and recovery", Journal of Thermal Biology, Sep. 2016, pp. 50-55, vol. 62, Elsevier, Amsterdam, Netherlands.

Geneva et al., "Normal Body Temperature: A Systematic Review", Open forum infectious diseases, Apr. 2019, pp. 1-7, 6(4), PubMed, Maryland, United States of America.

Kostopoulis et al., "A Machine Learning approach to Febrile Classification", Masters Theses, Apr. 25, 2018, 82 pages, Worcester Polytechnic Institute, Worcester, Massachusetts, United States of America.

Moràn-Navarro et al., "Validity of Skin, Oral and Tympanic Temperatures During Exercise in the Heat: Effects of Wind and Sweat." Annals of biomedical engineering, Aug. 2018, pp. 317-331, vol. 47, 1, Springer, Virginia, United States of America, Abstract.

Owen et al., Infrared thermography in paediatrics: a narrative review of clinical use, BMJ paediatrics open, Sep. 2017, pp. 1-10, vol. 1, 1, PubMed, Maryland, United States of America.

Priest et al., "Thermal Image Scanning for Influenza Border Screening: Results of an Airport Screening Study", PLoS One, Jan. 5, 2011, pp. 1-7, 6(1), Priest et al., Hong Kong, China.

Ring et al., "New Standards for Fever Screening with Thermal Imaging Systems", Chapter 5 of Infrared Imaging A Casebook in Clinical Medicine, Sep. 2015, pp. 5-1 to 5-11, IOP Publishing Ltd, Bristol, United Kingdom, Abstract.

Sherenshis, Michael, "Challenges to Global Implementation of Infrared Thermography Technology: Current Perspective", Central Asian journal of global health, Oct. 2017, 5 pages, vol. 6, 1, PubMed, Maryland, United States of America.

Sturdee et al., "Thermography of Menopausal Hot Flushes", Maturitas, Feb. 1979, pp. 201-205, vol. 1, 3, Elsevier, Amsterdam, Netherlands, Abstract.

Tay et al., "Comparison of Infrared Thermal Detection Systems for Mass Fever Screening in a Tropical Healthcare Setting", Public health, Aug. 2015, pp. 1471-1478, 129(11), Elsevier, Amsterdam, Netherlands.

* cited by examiner

NON-CONTACT TEMPERATURE MEASUREMENT IN THERMAL IMAGING SYSTEMS AND METHODS

CROSS-REFERENCE TO RELATED APPLICATIONS

This application is a continuation of International Patent Application No. PCT/US2021/026060 filed Apr. 6, 2021 and entitled "NON-CONTACT TEMPERATURE MEASUREMENT IN THERMAL IMAGING SYSTEMS AND METHODS," which claims priority to and the benefit of U.S. Provisional Patent Application No. 63/006,063 filed Apr. 6, 2020 and entitled "NON-CONTACT TEMPERATURE MEASUREMENT IN THERMAL IMAGING SYSTEMS AND METHODS," and U.S. Provisional Patent Application No. 63/090,691 filed Oct. 12, 2020 and entitled "NON-CONTACT TEMPERATURE MEASUREMENT IN THERMAL IMAGING SYSTEMS AND METHODS," all of which are hereby incorporated by reference in their entirety.

TECHNICAL FIELD

One or more embodiments of the present disclosure relate generally to non-contact temperature measurement, and more particularly, for example, to systems and methods for receiving and processing thermal data for use in health screening applications.

BACKGROUND

Thermal cameras can be used to measure the surface temperature of people to help identify individuals who have a fever. Thermal cameras work reasonably well in certain controlled environments, but face challenges when deploying non-contact thermal measurement systems in public spaces, crowded environments, and other environments where people move freely. Additional problems arise in critical applications, such as identifying fevered individuals during a pandemic, where real-time processing, adapting to changing environments, and accurate determinations are important to avoid falsely identifying individuals (false positives) or missing infected individuals (false negatives).

For example, individual screening with thermal cameras can create bottlenecks, causing delays in moving people and leaving the queued people to position closer in contact with each other. This bottleneck can increase the risk of infection transmission in high traffic areas such as airports and train stations. In some situations, it is desirable to monitor people in groups or crowds such as workplaces (offices, manufacturing floors), classrooms, public transportation, courtrooms, or other places where a population of people could be subject to infection or re-emergence of an epidemic/pandemic (such as seasonal flu).

In view of the foregoing, there is a continued need in the art for improved systems and methods for non-contact temperature measurement.

SUMMARY

Improved systems and methods for non-contact temperature measurement are described herein. The scope of this disclosure is defined by the claims, which are incorporated into this section by reference. A more complete understanding of embodiments of the disclosure will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the disclosure and their advantages are best understood by referring to the detailed description that follows. It should be appreciated that like reference numerals are used to identify like elements illustrated in one or more of the figures.

DETAILED DESCRIPTION

Figure 1A:
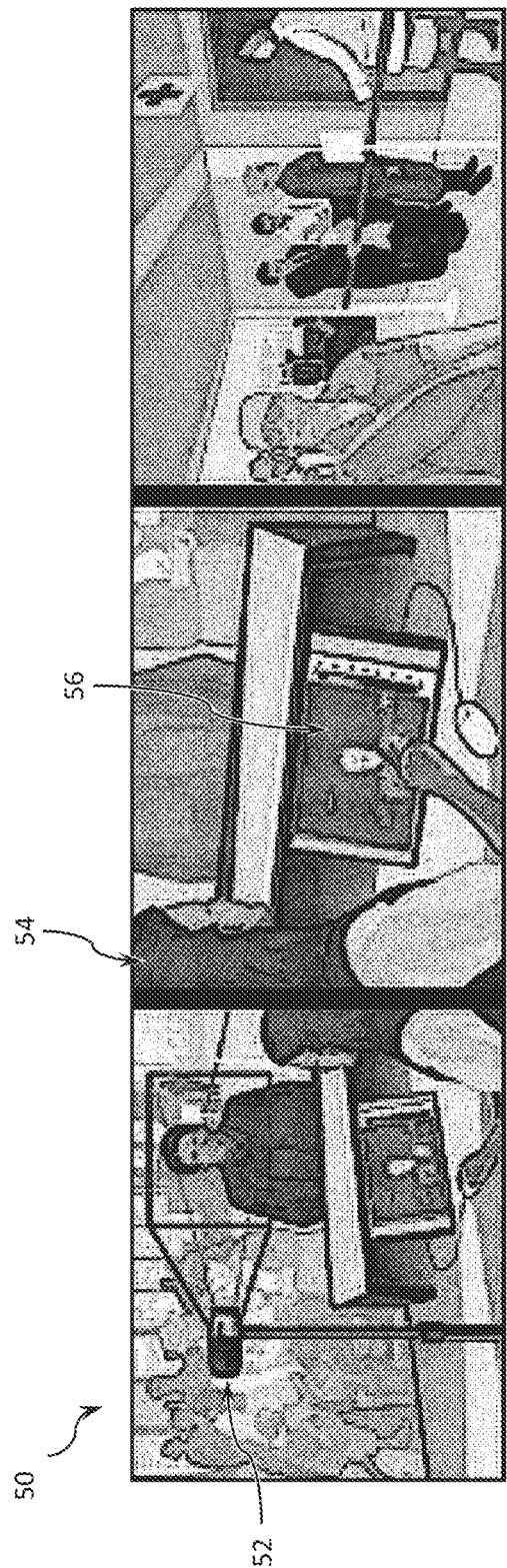
FIG. 1A illustrates an example thermal imaging system deployed at a checkpoint and configured to identify people with elevated temperatures, in accordance with one or more embodiments of the present disclosure.
Figure 1A:
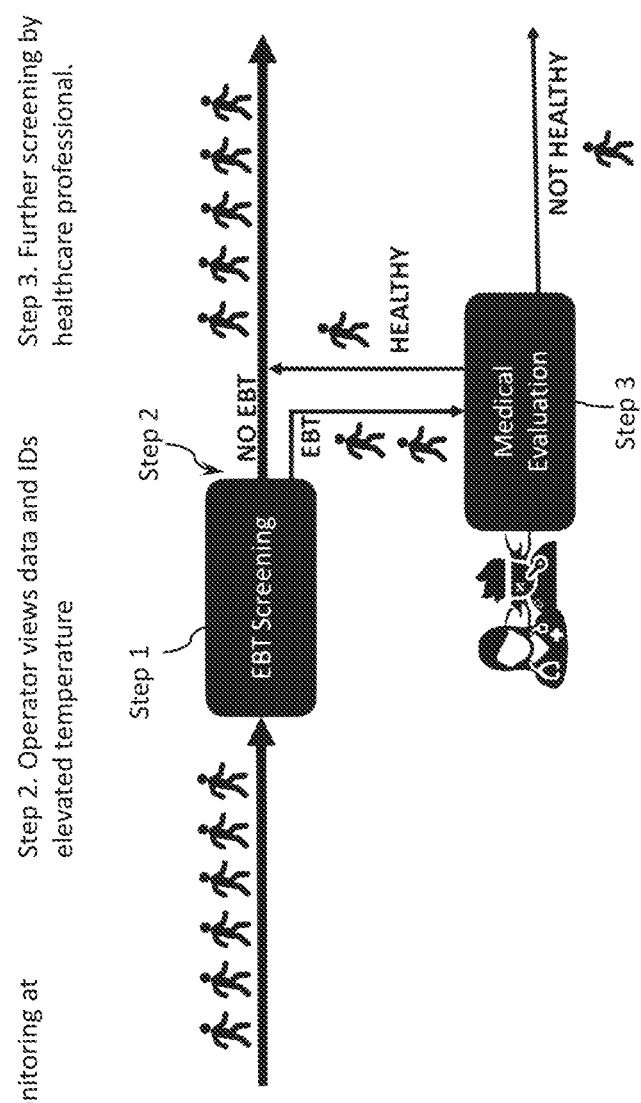

The present disclosure, in accordance with various embodiments, describes improved systems and methods for non-contact temperature measurement. Various systems and methods disclosed herein may be used with thermal cameras (e.g., handheld thermal cameras, thermal cameras in a fixed location, etc.) for individual screening, systems deployed to provide real-time screening of people in a variety of environments, including crowds and high traffic areas, and other temperature measurement systems for detecting elevated skin or body temperature.

The present disclosure improves processing and accuracy and may be used for critical scenarios, such as monitoring and controlling people with infectious diseases during an epidemic or pandemic (e.g., monitoring virus spread during a global outbreak of a coronavirus, such as COVID-19). Detecting, tracking, and containing the spread of an infectious disease is often a priority of governments and healthcare professionals to help slow and contain the spread of a virus. In some embodiments disclosed herein, a thermal imaging system may be positioned in high-traffic places to provide quick screening for detecting individuals who have a fever. Thermal images and/or other data are analyzed using machine learning to detect, tag and track people in the crowd, identify a person's head position, identify facial features (e.g., the person's forehead), and obtain a temperature measurement on the person's forehead, corner of their eye, or other desired location. In some embodiments, zoom optics are used to target a particular temperature measurement location on a person being tracked.

Thermal Imaging for Virus/Infection Monitoring

In various embodiments, thermal imaging technology is described that can be utilized to rapidly identify individuals with fevers within large crowds in support of increased surveillance and security measures, as well as prioritization of monitoring and response assets. The technology may be used by governments, health care providers, public/private businesses, individuals and/or other entities to provide heightened situational awareness across multiple mission areas. In some embodiments, a thermal imaging device is configured to capture panoramic, high-resolution thermal images that are analyzed using a machine learning system that enables autonomous measurement of the temperatures of populations of people. The thermal imaging device may be configured to rapidly identify an individual that may have an elevated temperature with the goal, for example, of isolating the individual from a crowd and/or preventing entrance by the individual to a crowd and prioritizing the individual for follow on diagnostic screening.

The embodiments disclosed herein help improve situational awareness enabling real-time, active tracking of potential public transmission of illnesses, such as COVID-19. The spread of an illness may be seasonal (e.g., the flu season typically encompasses winter months) and may wane due to a variety of factors including effective mitigation approaches, demographics, immunity, and other factors. The potential for resurgence before an effective vaccine is approved leaves an enormous vulnerability to populations, even when it may appear that illness is contained. The systems and methods disclosed here provide a novel thermal imaging platform that provides persistent, presumptive surveillance of vulnerable populations to rapidly identify and prevent the reemergence of illnesses, including during the period before a vaccine is complete and widely distributed.

In one implementation, a system is designed to protect a specified population of interest. The system may be deployed in a workplace (e.g., factories, hospitals, etc.), schools, stores, homes and other locations. A thermal camera is placed to continually monitor the premises and target early detection of people (or other desired objects) meeting particular criteria. The system may be configured to provide situational awareness by prioritizing assets to support and assist in treatment of illnesses and minimize the impact of spread.

In another implementation, a system is configured to protect a location by screening people at points of entry (POE) to target and take measures to keep out potentially sick people. The system may be deployed, for example, at mass transit locations such as airports, train stations and subway stations, cruise ships, entertainment venues (e.g., arenas, theaters), and other locations. The system may be configured to minimize potential contamination through a high-speed processing system that automates the screening a high volume of people. In some embodiments, the system captures thermal images, tags people and other objects of interest, and tracks the location of tagged people and objects through one or more scenes.

Embodiments of the present application will now be described in further detail with respect to FIGS. 1A, 1B and 1C. FIG. 1A illustrates an example thermal imaging system deployed at a checkpoint, configured to provide surveillance of large crowds to identify people with elevated temperatures that may indicate fevers. Fevers often present as early symptoms of infection, and temperature detection has been deployed in many airports and other public transportation settings in order to try to screen and/or sequester people who may be infected with a virus. Temperature measurements may be used in cursory screening triage techniques in a global healthcare crisis to support prioritization of critical medical assets.

As shown in FIG. 1A, a system 50 incorporating a high-resolution thermal camera 52 may be utilized at screening checkpoints for passenger screening in transportation hubs. Thermal imaging at screening checkpoints can be used as an adjunctive tool to aide in the identification of people who may have fevers and require further diagnostic screening by a healthcare professional. In Step 1 of the illustrated example, the system 50, including the high-resolution thermal camera 52 is deployed to provide remote monitoring of people at one or more checkpoints. In Step 2, an operator 54 views data on a display 56 and an identification of elevated temperature as determined by the thermal imaging system 50. If the person being screened is determined to have a fever, then in Step 3, the person is directed to move to a second location for further screening (e.g., by a healthcare professional). If there is no detected elevated temperature, at either the first checkpoint or second screening location, then the person can pass through the checkpoint. Otherwise, the person may be determined to be unhealthy and a risk to infect others and blocked from passing through the checkpoint. In some embodiments, the thermal camera 52 is integrated as security checkpoints in a handheld device with high temperature resolution for use as a mobile adjunctive diagnostic tool, such as by screening for differences in skin surface temperatures.

Figure 1B:
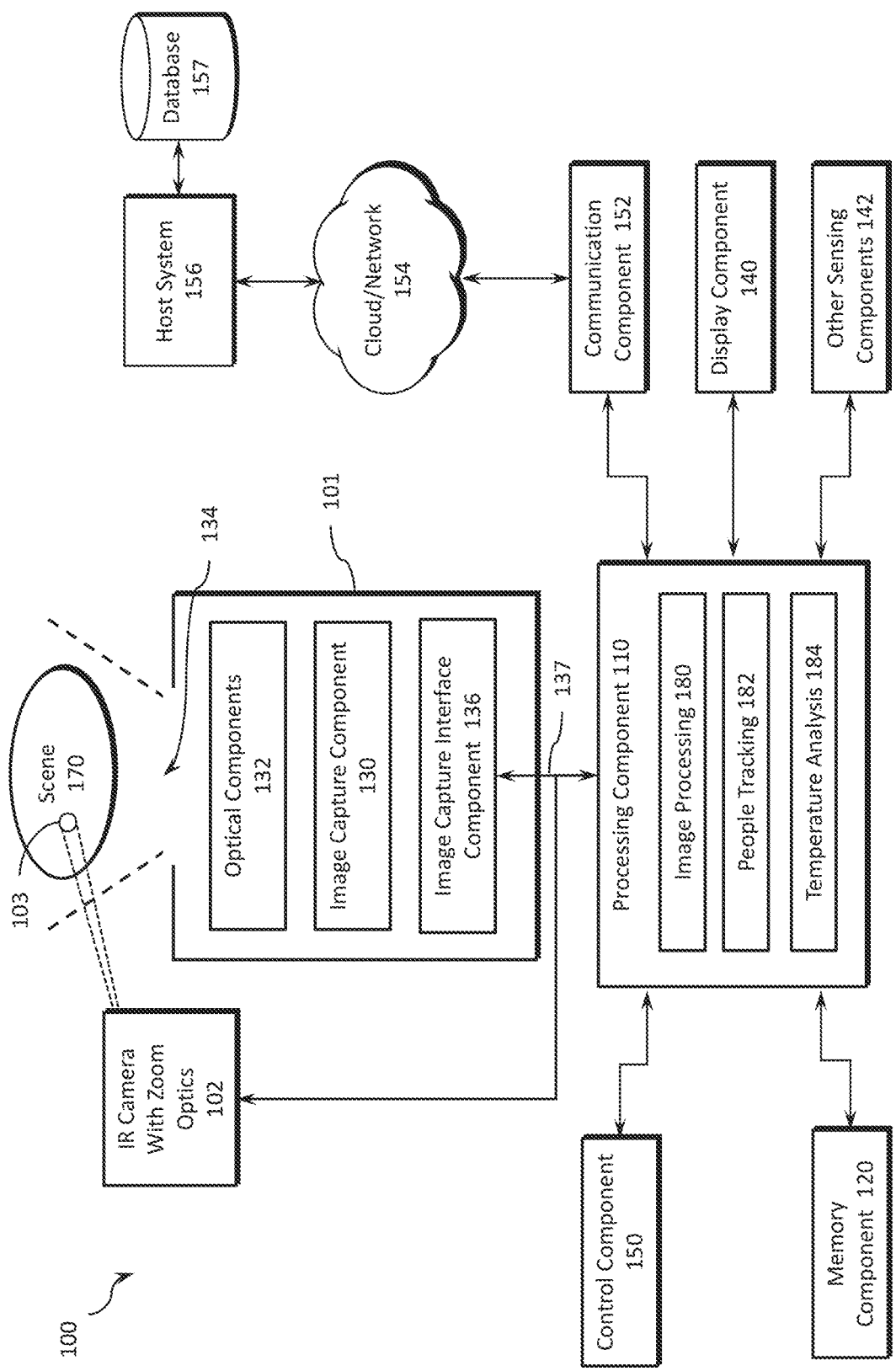
FIG. 1B illustrates an example thermal imaging system, in accordance with one or more embodiments of the present disclosure.

Referring to FIG. 1B. an example thermal imaging system 100 that may be used for infectious disease monitoring will now be described, in accordance with one or more embodiments. The thermal imaging system 100 may be used to capture and process thermal images to identify, track, and monitor the temperature of people in a scene 170. As illustrated, the thermal imaging system 100 may be used for imaging the scene 170, which is within in a field of view of the thermal imaging system 100. The thermal imaging system 100 includes a processing component 110, a memory component 120, an image capture component 130, optical components 132 (e.g., one or more lenses configured to receive electromagnetic radiation through an aperture 134 in camera component 101 and pass the electromagnetic radiation to image capture component 130), an image capture interface component 136, a display component 140, a control component 150, a communication component 152, and other sensing components 142.

In various embodiments, thermal imaging system 100 may be implemented as a handheld thermal imaging device and/or a stationary thermal imaging device that includes the camera component 101 to capture image frames, for example, of the scene 170 in the field of view of camera component 101. In some embodiments, the camera component 101 may include the image capture component 130, optical components 132, and the image capture interface component 136 housed in a protective enclosure. Thermal imaging system 100 may represent any type of camera system that is adapted to image the scene 170 and provide associated thermal image data. Thermal imaging system 100 may be implemented with camera component 101 at various types of fixed locations and environments (e.g., airport, event venue, office building, etc.). In some embodiments, camera component 101 may be mounted in a stationary arrangement to capture successive images of a scene 170. In some embodiments, the thermal imaging system 100 may include a portable device and may be implemented, for example, as a handheld device and/or coupled, in other examples, to various types of portable devices and/or vehicles (e.g., a land-based vehicle, a watercraft, an aircraft, a spacecraft, or other vehicle).

The processing component 110 may include, for example, a microprocessor, a single-core processor, a multi-core processor, a microcontroller, a logic device (e.g., a programmable logic device configured to perform processing operations), a digital signal processing (DSP) device, one or more memories for storing executable instructions (e.g., software, firmware, or other instructions), and/or any other appropriate combination of processing device and/or memory to execute instructions to perform any of the various operations described herein. Processing component 110 is adapted to interface and communicate with components 101, 102, 120, 140, 142, 150 and 152 to perform method and processing steps as described herein. Processing component 110 is also adapted to detect and classify objects in the images captured by the image capture component 130, through image processing module 180, people tracking module 182, and temperature analysis module 184.

It should be appreciated that processing operations and/or instructions may be integrated in software and/or hardware as part of processing component 110, or code (e.g., software or configuration data) which may be stored in memory component 120. Embodiments of processing operations and/or instructions disclosed herein may be stored by a machine-readable medium in a non-transitory manner (e.g., a memory, a hard drive, a compact disk, a digital video disk, or a flash memory) to be executed by a computer (e.g., logic or processor-based system) to perform various methods disclosed herein.

Memory component 120 includes, in one embodiment, one or more memory devices (e.g., one or more memories) to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, or other types of memory. In one embodiment, processing component 110 is adapted to execute software stored in memory component 120 and/or a machine-readable medium to perform various methods, processes, and operations in a manner as described herein.

Image capture component 130 includes, in one embodiment, one or more sensors for capturing image signals representative of an image of scene 170. In one embodiment, the sensors of image capture component 130 provide for representing (e.g., converting) a captured thermal image signal of scene 170 as digital data (e.g., via an analog-to-digital converter included as part of the sensor or separate from the sensor as part of thermal imaging system 100). The thermal sensors may include a plurality of infrared sensors (e.g., infrared detectors) implemented in an array or other fashion on a substrate. For example, in one embodiment, infrared sensors may be implemented as a focal plane array (FPA). Infrared sensors may be configured to detect infrared radiation (e.g., infrared energy) from a target scene including, for example, mid wave infrared wave bands (MWIR), long wave infrared wave bands (LWIR), and/or other thermal imaging bands as may be desired in particular implementations. Infrared sensors may be implemented, for example, as microbolometers or other types of thermal imaging infrared sensors arranged in any desired array pattern to provide a plurality of pixels.

Processing component 110 may be a logic device adapted to receive image signals from image capture component 130, process image signals (e.g., to provide processed image data), store image signals or image data in memory component 120, and/or retrieve stored image signals from memory component 120. In various aspects, processing component 110 may be remotely positioned, and processing component 110 may be adapted to remotely receive image signals from image capture component 130 via wired or wireless communication with image capture interface component 136, as described herein.

Display component 140 may include an image display device (e.g., a liquid crystal display (LCD)) or various other types of generally known video displays or monitors. Control component 150 may include, in various embodiments, a user input and/or interface device, such as a keyboard, a control panel unit, a graphical user interface, or other user input/output. Control component 150 may be adapted to be integrated as part of display component 140 to operate as both a user input device and a display device, such as, for example, a touch screen device adapted to receive input signals from a user touching different parts of the display screen.

Processing component 110 may be adapted to communicate with image capture interface component 136 (e.g., by receiving data and information from image capture component 530). Image capture interface component 136 may be configured to receive image signals (e.g., image frames) from image capture component 130 and communicate image signals to processing component 110 directly or through one or more wired or wireless communication components (e.g., represented by connection 137) in the manner of communication component 152 further described herein. Camera component 101 and processing component 110 may be positioned proximate to or remote from each other in various embodiments.

Communication component 152 may be implemented as a network interface component adapted for communication with a cloud/network 154 including other devices in the network and may include one or more wired or wireless communication components. In various embodiments, the cloud/network 154 may be implemented as a single network or a combination of multiple networks, and may include a wired or wireless network, including a wireless local area network, a wide area network, the Internet, a cloud network service, and/or other appropriate types of communication networks.

In various embodiments, the thermal imaging system 100 provides a capability, in real time, to detect, track and determine a temperature of people in the scene 170. For example, thermal imaging system 100 may be configured to capture images of scene 170 using camera component 101 (e.g., an infrared camera). Captured images may be received by processing component 110 and stored in memory component 120. The image processing module 180 and people tracking module 182 may extract from each of the captured images a subset of pixel values of scene 170 corresponding to a detected person. The temperature analysis module 184 analyzes available information to estimate the temperature of the tracked people and stores the result in the memory component 120, a database or other memory storage in accordance with system design preferences. In some embodiments, the thermal imaging system 100 may send thermal image data or other sensed, calculated and/or determined data over the network 154 (e.g., the Internet or the cloud) to a host system 156 and database 157 for remote processing and/or storage.

The people tracking module 182 and temperature analysis module 184 are configured to provide analysis of the captured thermal images and other data to detect people, track people and determine a person's temperature. The people tracking module 182 may further include other people counting and tracking functionality, for example, to measure traffic flow through an area corresponding to the scene 170. In various embodiments, the people tracking module 182 interfaces with one or more databases and/or other sensors, which provide additional data for detecting/tracking people and determining their temperature. For example, the database may store criteria for identifying people, reference images of known conditions, field of view parameters for each image capture device (e.g., to for use in estimating size and location of detected people and objects), learned and configured activities common to the image capture device, and other people tracking information.

The temperature analysis module 184 analyzes one or more thermal images of a tracked person to determine the person's temperature. In some embodiments, the temperature analysis module 184 is configured to detect a measurement location on a tracked person, instruct the camera component 101 to zoom in on the desired location (e.g., via optical or digital zoom components, such as infrared camera with zoom optics 102) and capture a thermal image of the measurement location. The temperature analysis module 184 may further receive other sensed data form other sensing components 142, and system data relating to system and environmental parameters. In some embodiments, face recognition is used to identify faces at different angles and/or distances and then find the best spot to measure the person's temperature.

The other sensing components 142 may include environmental and/or operational sensors, depending on the sensed application or implementation, which provide information to processing component 110 (e.g., by receiving sensor information from each sensing component 142). In various embodiments, other sensing components 142 may be adapted to provide data and information related to environmental conditions, such as internal and/or external temperature conditions, lighting conditions (e.g., day, night, dusk, and/or dawn), humidity levels, specific weather conditions (e.g., sun, rain, and/or snow), distance (e.g., laser rangefinder), ambient sound, visible image sensors, and/or other sensor types. Accordingly, other sensing components 142 may include one or more conventional sensors as would be known by those skilled in the art for monitoring various conditions (e.g., environmental conditions) that may have an effect (e.g., on the image appearance) on the data provided by image capture component 130.

In some embodiments, an infrared camera with zoom optics 102 is provided to provide accurate thermal temperature measurements of a target 103 in the scene 170. The camera component 101 may comprise a wide field-of-view (FOV) infrared (IR) microbolometer camera providing 360-degree imaging for identifying people in a wide scene 170 by running neural network algorithms that identify and track a person in the scene. After a person is identified by the people tracking component 182, the paired IR camera with zoom optics 102 is instructed to focus on the target 103 and take a series of temperature measurements that will be analyzed by an algorithm to determine the number of data points required over time and set a threshold for deviation that triggers an alarm. The system will then report (e.g., to another system, to the person monitoring, etc.) that a subject should be isolated for further diagnostic evaluation by a medical professional.

In some embodiments, the camera component 101 is a visible light camera configured and the people tracking module 182 us configured to perform face recognition on captured images and determine where in the scene 170 faces are located. A thermal camera, such as paired IR camera with zoom optics 102, is aligned and calibrated with the visible light camera to identify areas in the thermal image where the faces are located. In various embodiments, the field of view of the visible light camera is at least as large as the paired thermal camera. The alignment of captured images is facilitated by accurately calibrating differences in pointing error, rotation, field of view and distortion between the two cameras. By limiting the measurements in the thermal image to location where it is known to be a face, the temperature measurement can be made more reliable. In some embodiments, cases where the face is obscured or there are heated areas that are not faces may be rejected.

In some embodiments, the thermal camera is calibrated to a known temperature and may be capable of determining the absolute temperature of the scene 170. The two cameras may further be (factory) calibrated to allow mapping a pixel in one camera to a pixel in the other camera. In some embodiments, the parameters to be determined relative to the cameras include pointing difference (pan/tilt), rotation difference (roll), difference in FOV (zoom) and/or difference in distortion. These differences can be determined in a factory calibration process. Also, the distance between the two cameras (parallax) may be a parameter used by the system for calibration and, in some embodiments, is configured to be as small as possible.

The people tracking module 182 is configured to detect size and orientation of the faces, as well as other varying factors such as glasses, face masks, beard etc. From the recognized and identified faces the corresponding location in the thermal image can be inferred using the above-mentioned calibration terms. In the thermal image, temperature can be measured at the location where faces are known to be, and at a target location of the face where the measurement yields the most accurate temperature. The visual face recognition can be used to avoid false measurements of objects that are close to human skin temperature but not actually humans. It can be used to track a person through the field of view and measure skin temperature at a moment when the orientation of the face relative to the camera(s) is expected to produce an accurate result.

Other sensing components 142 may include devices that relay information to processing component 110 via wireless communication. For example, each sensing component 142 may be adapted to receive information from a satellite, through a local broadcast (e.g., radio frequency) transmission, through a mobile or cellular network and/or through information beacons in an infrastructure or various other wired or wireless techniques.

In various embodiments the thermal imaging system is configured to achieve high accuracy and reduce measurement errors using one or more systems and methods described herein, which factor in the distance from the target to the thermal camera, capture and analysis of a high resolution image of the target (e.g., systems and methods for increasing the number of pixels on the target), identification of areas on target to take measurement from, time on the target for measuring and tracking, calibration of the system in the field, presence of a black body in the field of view or radiometric calibration, access to areas of interest on the target (e.g., tear ducts), time for the temperature of settle after entering field of view (e.g., if the target enters from outside the target temperature may need time to adjust to the new setting), and/or other factors.

Figure 1C:
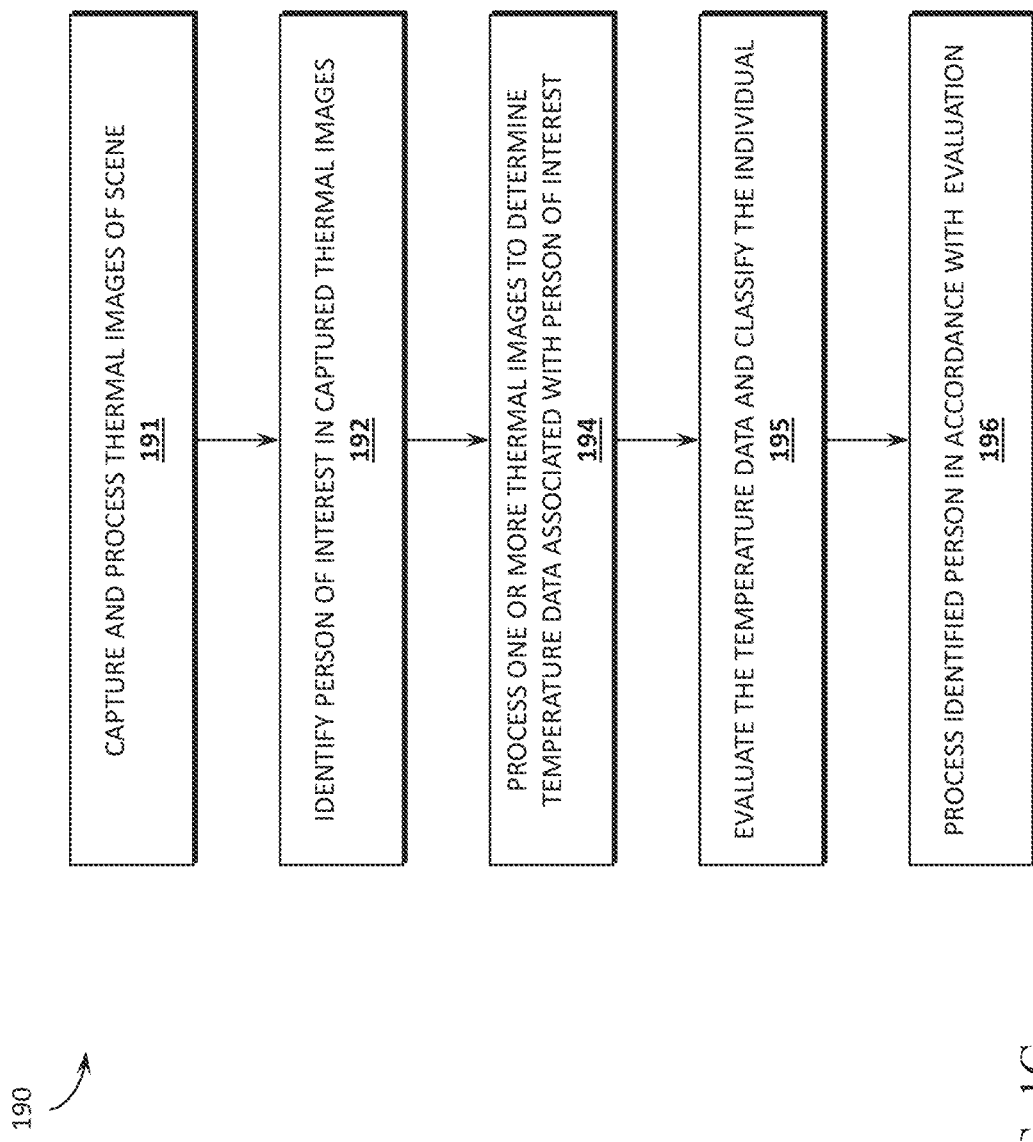
FIG. 1C illustrates an example operation of a thermal imaging system, in accordance with one or more embodiments of the present disclosure.

Referring to FIG. 1C, an example operation of a thermal imaging system (e.g., thermal imaging system 100) will now be described, in accordance with one or more embodiments. The systems and methods described herein provide improved reliability and accuracy over conventional techniques for detecting elevated body and/or skin temperature. In some embodiments, the techniques are applied person-to-person (e.g., relative to other people) to improve performance over absolute temperature comparisons which fail to account for variable environmental conditions and the average temperature of persons in the scene. In some embodiments, the elevated body temperature detection described herein does not require a black body in the scene for calibration, but can optionally use a black body when desired, which improves flexibility of deployment over conventional systems. The systems and methods described herein can compensate for multiple factors including distance from camera and person-to-person differences.

In the illustrated embodiment, a process 190 begins by capturing and processing thermal image of a scene, in step 191. The thermal images can be captured in real-time to monitor crowds and/or captured and stored for later processing. In some embodiments, other data is also captured, such as a visible light image which may be aligned with the thermal image to help identify humans, audio, time, date, location, temperature, and other data. The thermal images are captured by a thermal camera that may be deployed at crowd flow choke points and/or other locations suitable for capturing thermal images of a person for temperature measurement as described herein.

In step 192, the captured thermal images are processed to identify a person of interest. People within an image are detected and tracked, and the system is configured to identify one or more tracked people for further temperature detection processing. In some embodiments, motion statistics between frames of the captured thermal images are used to identify people who are moving in the scene. In other embodiments, a trained convolutional neural network (or other machine learning module) is configured to receive one or more thermal images and identify people in the image. The system may further be configured to identify a location of a person in the image (e.g., identifying a bounding box surrounding that person), a size of the person. One or more identified people will then be separately selected to for further processing to determine the person's temperature. The system may use automatic person identification, a person may self-identify by interacting with a kiosk, user guided identification may be used to direct the system to focus on certain individuals, and/or other person identification techniques may be used.

In step 194, the system processes one or more thermal images to determine temperature data associated with the person of interest. In some embodiments, the system uses the captured images from step 191 to measure the user's temperature. In other embodiments, the person of interest is tracked by the system to identify a thermal image capture opportunity, such as visible forehead in the image and/or an eye in the image. The system may be instructed to capture images, zoom into the person and capture images, and/or perform other image capture steps. After the thermal image is captured, the thermal image is processed to identify a location for taking the measurement and determine the temperature at the measurement location. In some embodiments, step 194 includes operating a neural network to identify humans in the crowd and determine a measurement location associated with each individual (e.g., forehead). The system may then perform a targeted zoom (e.g., optical zoom, digital zoom, etc.) onto the measurement location and capture a new thermal image for use in measuring the person's temperature.

In various embodiments, the system is configured to process one or more thermal images and/or other data to determine and/or estimate the person of interest's core temperature. The processing may include detecting a skin temperature and using the skin temperature to determine the person's core body temperature. For example, skin temperature may settle within 4-5 minutes, providing a correlation with core body temperature. In some embodiments, the thermal image is captured using a high definition thermal camera, which is configured for an accuracy range within 0.1 degree 80% of time and within 0.2 degree 100% of time, allowing the system to accurately detect small changes in person-to-person temperature. In various embodiments, the scene is processed as a black body for measurement using a low-cost process.

In some embodiments, the system uses multiple measurement points to estimate core body temperature. An automated algorithm may be used for updating temperature distributions. Other measurement techniques may include user temperature offset feature to increase measurement accuracy, and/or stereo thermal imaging for depth map and monitoring system drift (e.g., distance compensation). Various camera parameters and processing parameters can be adjusted or compensated to improve temperature accuracy, including distance of target, image resolution, areas on target to take measurement from, time on target, in-field calibration, use of blackbody or radiometric calibration, particular areas of interest (e.g., forehead, tear ducts), time for target temperature to settle, etc. In various embodiments, the parameters are processed to extract features for input to a neural network trained to identify a core body temperature and/or other temperature-related data.

Next, the system evaluates the temperature data associated with the person of interest and classifies the individual, in step 195. In various embodiments, the temperature data is evaluated to determine whether the person of interest has an elevated body temperature. In some embodiments, a direct reading from a thermal camera at a measurement location is used. In other embodiments, the system evaluates other available data to obtain more accurate classification results. For example, the system may process the captured thermal images to determine an average temperature measurement for humans passing through the scene (e.g., to adjust subsequent thermal image processing of person of interest in response to temporal changes in temperature associated with environmental conditions). The system may be configured to group persons by criteria such as by age (e.g., young children, older adults, etc.) to provide an accurate assessment of an average temperature for each grouping. The grouping may be based, for example, on a face recognition process that determines an approximate age. The temperature data may be compared to a baseline number, adjusted based on other data and criteria, processed through a neural network, and/or other processing may be performed.

Figure 1D:
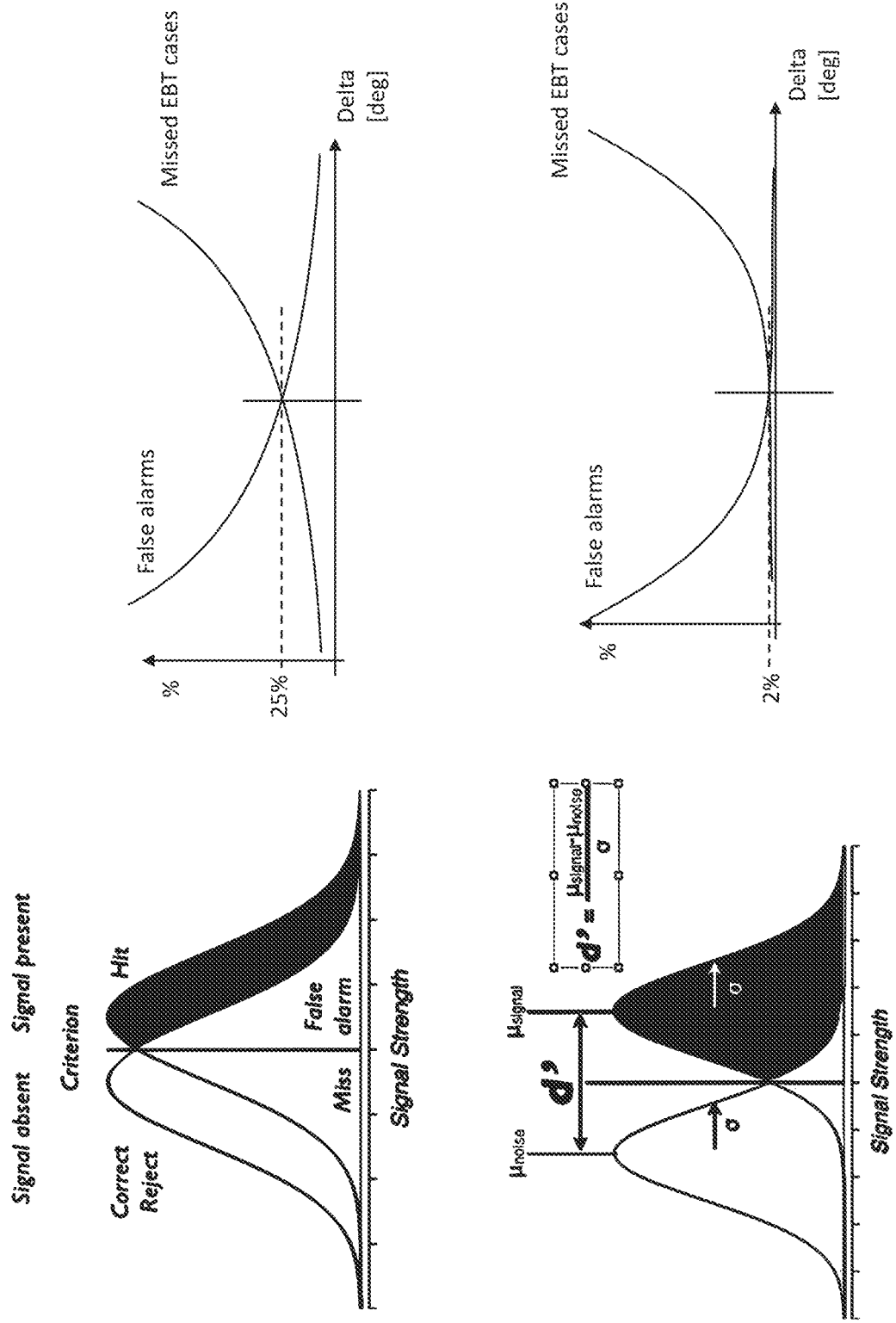
FIG. 1D illustrates delta considerations for avoiding false positives and false negatives, in accordance with one or more embodiments.

In various embodiments, the system compares the person of interest's estimated core body temperature and/or measured skin temperature (or other spot temperature, such as an eye) to an average temperature of other persons who are statistically similar. In some embodiments, a neural network may be trained to classify detected people into groups (e.g., by age range, gender, size). Each class of people may have its own temperature model, which allows the system to adjust temperature data on the fly to limit the number of false positives and/or false negatives for a more accurate model. This group adjusted measurements may be combined with other adjustments described herein, such as a person's tracked travel path through areas monitored by the system (e.g., temperature changes as a person enters a building) or changes in temperature over time. In some embodiments, the temperature data models may be provided as input to trained neural network and/or statistical analysis process to determine an adjusted temperature for a person. In various embodiments, the system is trained/configured with an appropriate delta between a baseline temperature (e.g., based on average of people in the scene, distance, people grouping such as an age range, travel path, etc.) based on and an EBT determination to avoid false positives or missing persons with EBT (see, e.g., FIG. 1D). In some embodiments, the process includes isotherm data for the scene coupled to an alarm threshold.

In step 196, the person of interest is then processed according to the evaluation. For example, if the person has a normal temperature, information about the individual may be stored for further statistical analysis, to train the system, or for other processing. If the person is determined to have an elevated body temperature (EBD), then the further processing may be performed based on the classification. In some systems, the information is stored for further analysis. In other systems, a user of the system is notified of the EBD and the person of interest is directed to another location for follow up health screening and actions, such as testing for the illness, quarantining the person of interest, preventing the person of interest from entering a crowded location, and/or other actions.

Persistent Thermal Imaging for Virus/Infection Detection

Figure 2A:
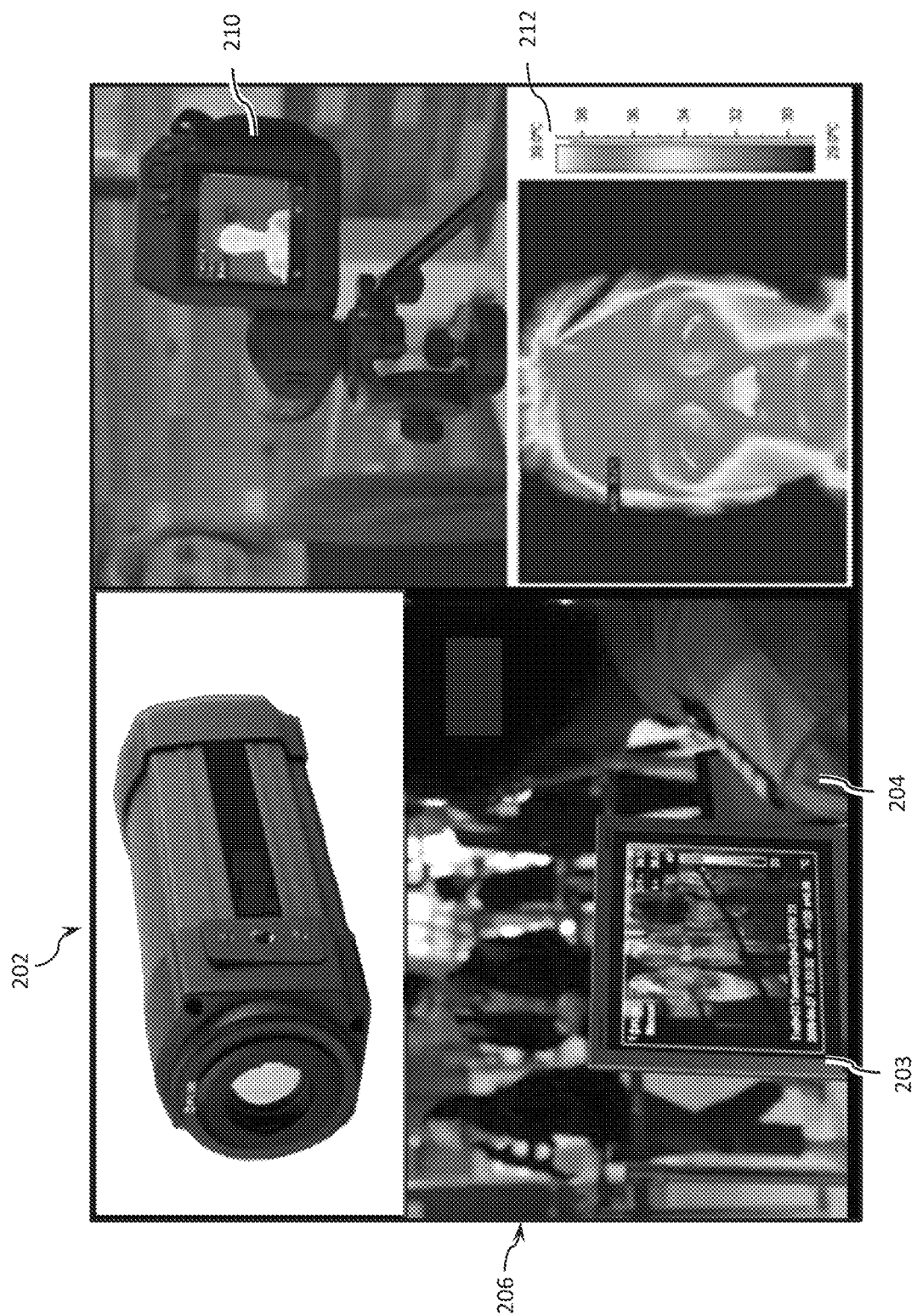
FIG. 2A illustrates example thermal imaging monitoring systems, in accordance with one or more embodiments of the present disclosure.

Pandemic response is an immense challenge for governments and society. An infectious disease may cause disruptions to businesses, schools, travel, public activities and other disruptions. The infections may grow through community spread for months or years before a vaccine is developed, if at all. High density deployment of monitoring devices may be used to rapidly identify people with fevers and isolate them from crowds quickly before they can infect others. Referring to FIG. 2A, monitoring devices such as thermal camera 202 and interactive user displays 203 may be used by security personnel 204 to rapidly screen travelers 206 for elevated temperatures indicative of possible fevers. A handheld camera 210 may also be used to provide high-resolution thermal imaging 212 over the skin.

In conventional systems, thermal cameras are typically integrated at security checkpoints through a person-in-the-loop approach, that is limited to screening one person at-a-time by security personnel. These approaches create significant backups in the crowd which can lead to even more direct contact among people that can spread of infection. Many diseases can be spread through airborne contamination with routine contact across community-spread, and the use of simple chokepoints and individual screening is not an effective way to manage and mitigate virus transmission.

In various embodiments of the present disclosure, an improved thermal camera platform incorporates novel machine learning approaches to screen large populations of individuals. The platform can be wirelessly connected to a monitoring network to enable rapid detection of new epidemic activity to provide early intervention to prevent growth and/or re-emergence of an infectious disease. Machine learning is used to identify people more efficiently in real-time in scenes, and to track them within large group for their surface temperatures to identify fever as early indicators of illness among individuals in a crowd.

Figure 2B:
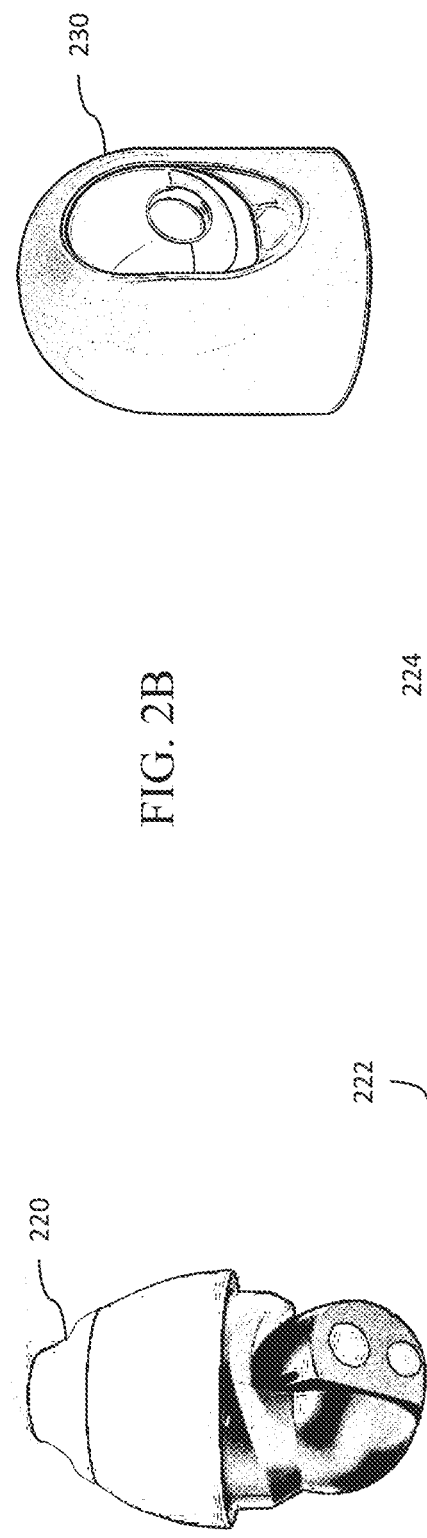
FIG. 2B illustrates example thermal camera form factors and an example implementation, in accordance with one or more embodiments of the present disclosure.
Figure 2C:
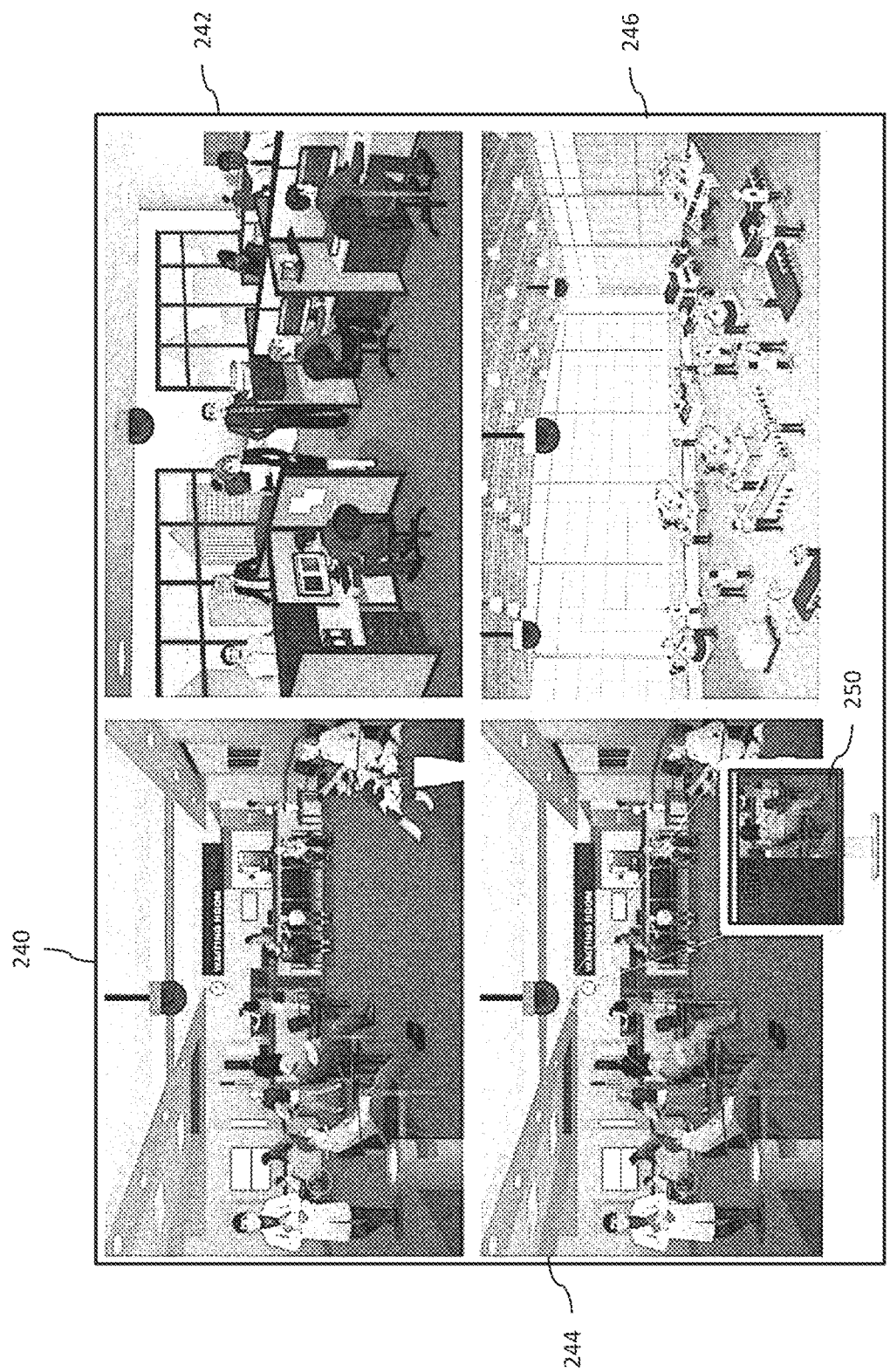
FIG. 2C illustrates example thermal camera implementations, in accordance with one or more embodiments of the present disclosure.

The thermal camera platform may have a form factor that is similar to ceiling or wall mounted smoke detector or thermal security camera. Examples of thermal imaging camera form factors are illustrated in FIG. 2B, including a thermal security camera 220 which may be used to capture infrared images of a crowd for fever screening as illustrated in image 222, and thermal security camera 230. In some embodiments, the thermal camera platform includes a wide field-of-view (FOV) infrared (IR) microbolometer camera providing 360-degree imaging for identifying people in a wide scene by running neural network algorithms that identify and track a person in the scene. These form factors support large stand-off distances and real-time large area monitoring. When a person is identified by the thermal camera, a paired IR camera with zoom optics will focus on the target and take a series of temperature measurements that will be analyzed by an algorithm to determine the number of data points required over time and set a threshold for deviation that triggers an alarm. The system will then report to the person monitoring that a subject should be isolated for further diagnostic evaluation by a medical professional. Referring to FIG. 2C, the thermal camera could be placed in a hospital waiting room 240 and signal an alarm on a display 250 when it detects a person with a fever (image 244). The thermal camera could also be deployed in an office setting 242 and manufacturing facility 246, for example.

Machine Learning for Virus/Infection Detection

Various aspects of the present disclosure may be implemented using trained neural networks and/or other machine learning processes including analysis of captured images to detect and locate people, identification of a measurement location on a person, determination of a person's core body temperature, and/or determination that an individual has a fever. Embodiments of neural networking systems and methods that may be used in the present disclosure will now be described with reference to FIGS. 3A-D.

Figure 3B:
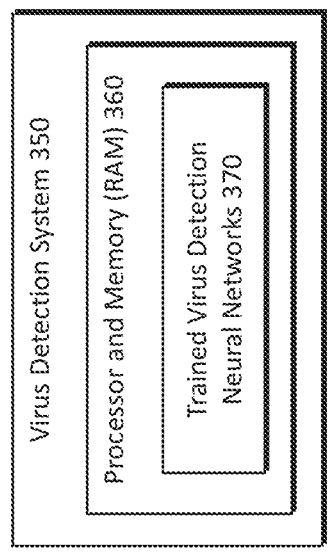
FIG. 3B illustrates an example of a remote virus detection system, in accordance with one or more embodiments of the present disclosure.
Figure 3A:
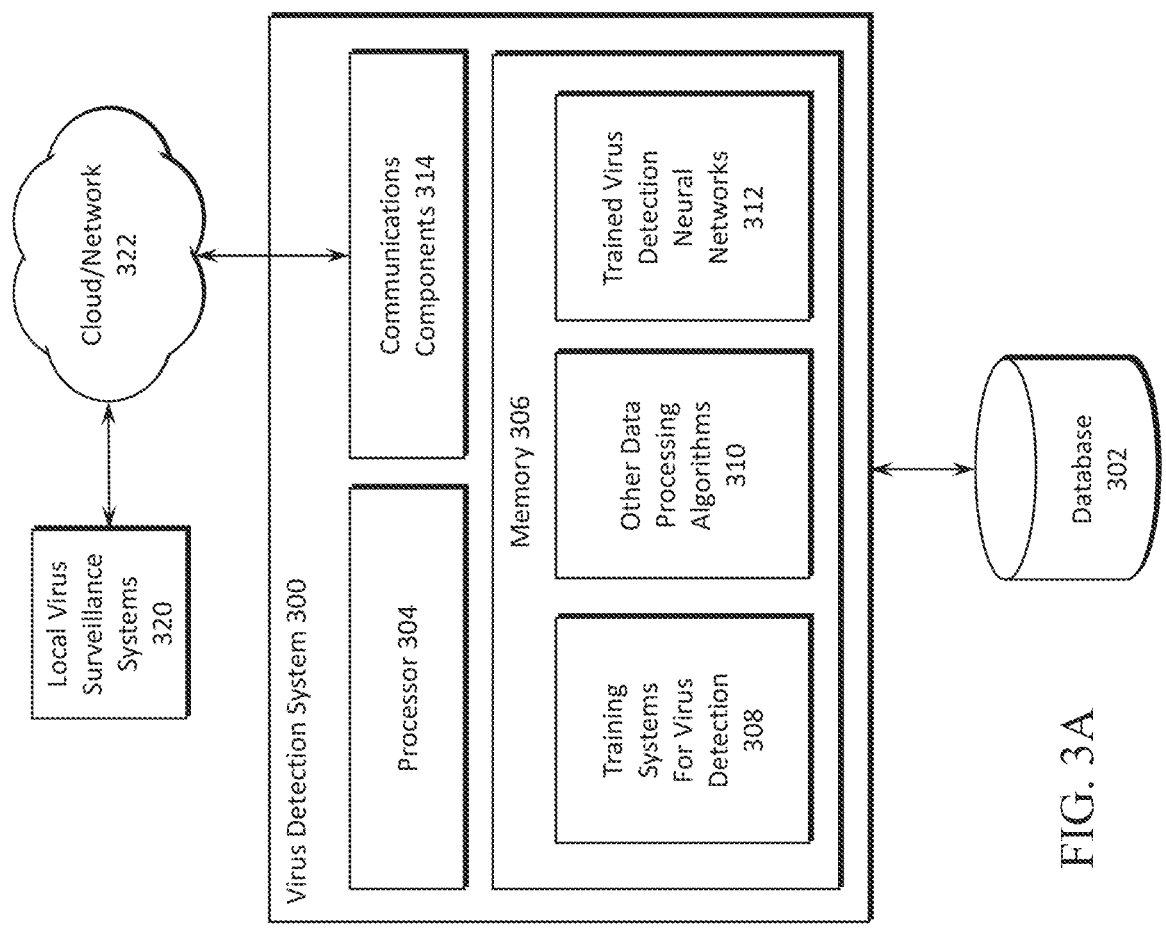
FIG. 3A illustrates an example virus detection system and network, in accordance with one or more embodiments of the present disclosure.

Referring to FIG. 3A, embodiments of a virus detection system will be described. The virus detection system 300 may be implemented on one or more servers such as an application server that performs data processing and/or other software execution operations for training, storing, and neural networks used by the virus detection system 300. In some embodiments, the components of the virus detection system 300 may be distributed across a communications network, such as cloud/network 322. The communications network 322 may include one or more local networks such as a wireless local area network (WLAN), wide area networks such as the Internet or cloud network, and other wired or wireless communications paths suitable for facilitating communications between components as described herein. The virus detection system 300 includes communications components 314 operable to facilitate communications with one or more local virus surveillance systems 320 over the communications network 322.

In various embodiments, the virus detection system 300 may operate as a networked virus detection system, such as a cloud-based virus detection system, or may be configured to operate in a dedicated system, such as a virus surveillance system that processes thermal images and other data captured in real time from one or more virus surveillance devices (e.g., a thermal imaging camera as described herein). The virus detection system 300 may be configured to analyze the captured data and return information regarding a virus determination (e.g., an alarm with an identification of an individual detected to have a fever). The virus detection system 300 may also include a database 302 for storing captured data, training datasets, and other information.

As illustrated, the virus detection system 300 includes one or more processors 304 that perform data processing and/or other software execution operations for the virus detection system 300. The processor 304 may include logic devices, microcontrollers, processors, application specific integrated circuits (ASICs), field programmable gate arrays (FPGAs) or other devices that may be used by the virus detection system 300 to execute appropriate instructions, such as software instructions stored in memory 306 including training systems for virus detection 308, other data processing algorithms 310, and trained virus detection neural networks 312 (e.g., a convolutional neural network trained by a training dataset stored in the database 302), and/or other applications.

The memory 306 may be implemented in one or more memory devices (e.g., memory components) that store executable instructions, data and information, including image data, video data, audio data, network information. The memory devices may include various types of memory for information storage including volatile and non-volatile memory devices, such as RAM (Random Access Memory), ROM (Read-Only Memory), EEPROM (Electrically-Erasable Read-Only Memory), flash memory, a disk drive, and other types of memory described herein.

Each local virus surveillance system 320 may be implemented as a computing device such as a thermal imaging camera, a handheld non-contact temperature sensing device, a desktop computer or network server, a mobile computing device such as a mobile phone, tablet, laptop computer or other computing device having communications circuitry (e.g., wireless communications circuitry or wired communications circuitry) for connecting with other devices in the virus detection system 300. In some embodiments, the local virus surveillance system 320 may include one or more unmanned vehicles (e.g., drones) such as an unmanned aerial vehicle, an unmanned ground vehicle, or other unmanned vehicle. An unmanned vehicle may be deployed, for example, to surveil a location while limiting operator infection, and may be configured with temperature sensors and processing systems to detect people and identify individuals with elevated body temperature. In some embodiments, the drone may include one or more loudspeaker to provide instructions or information to nearby people, distance sensors (e.g., laser), global positioning satellite components to determine location, navigation components, communications components for communication with a host system and/or operator, and other components for a desired used. Drones may be used to identify infected individuals in a public location, monitoring quarantines, and other scenarios where stationary and/or hand-held temperature monitoring is impractical.

The communications components 314 may include circuitry for communicating with other devices using various communications protocols. In various embodiments, communications components 314 may be configured to communicate over a wired communication link (e.g., through a network router, switch, hub, or other network devices) for wired communication purposes. For example, a wired link may be implemented with a power-line cable, a coaxial cable, a fiber-optic cable, or other appropriate cables or wires that support corresponding wired network technologies. Communications components 314 may be further configured to interface with a wired network and/or device via a wired communication component such as an Ethernet interface, a power-line modem, a Digital Subscriber Line (DSL) modem, a Public Switched Telephone Network (PSTN) modem, a cable modem, and/or other appropriate components for wired communication. Proprietary wired communication protocols and interfaces may also be supported by communications components 314.

One or more trained virus detection neural networks 370 may be implemented in a remote, real-time environment, as illustrated in FIG. 3B. The virus detection system 350 may include a thermal imaging camera or other device or system operable to receive and/or generate thermal images and process the received thermal images using one or more detection processes described herein. In the illustrated embodiment, the virus detection system 350 includes a processor and memory 360, operable to store one or more trained neural networks and implement a neural network run-time interface 370 thereon.

Figure 3C:
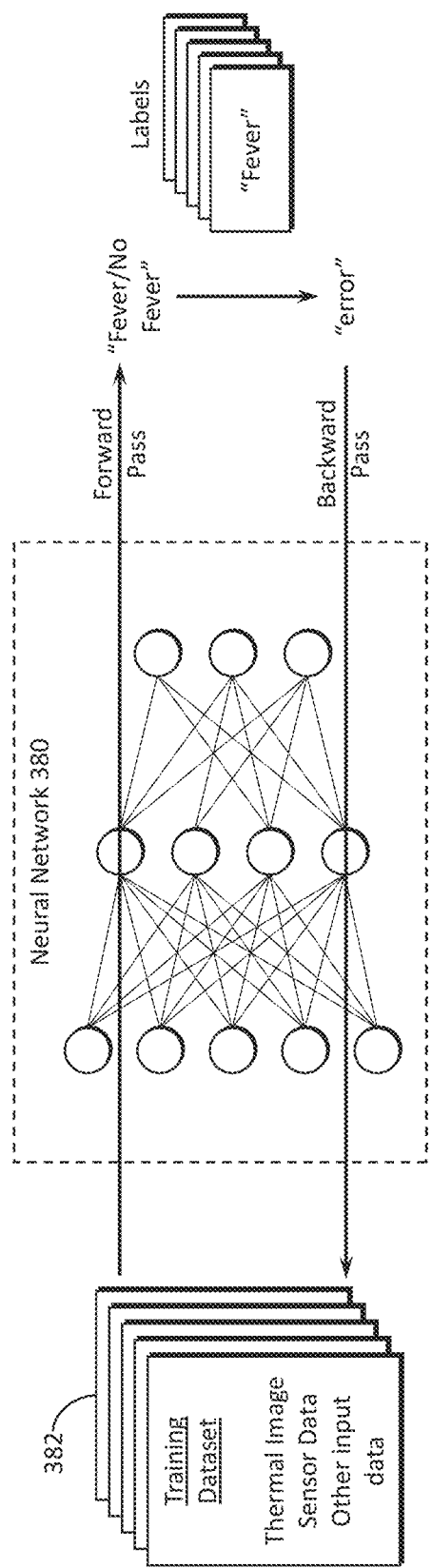
FIG. 3C illustrates an example virus detection training process, in accordance with one or more embodiments of the present disclosure.

In various embodiments, a training dataset with virus detection information may be used to train one or more neural networks and/or other machine learning algorithms for use in a virus detection system. Referring to FIG. 3C, an embodiment of a neural network training process will now be described. In one embodiment, the neural network 380 is a convolutional neural network (CNN) that receives the training dataset 382 that includes up-to-date virus detection information and outputs a classification for the data. The present disclosure describes a plurality of neural networks that may be trained for one or more determinations of the virus detection system, including but not limited to, detecting and tracking people in a crowd from visible light and/or thermal images, detection of a temperature measurement location on an individual, detection of an individual's temperature (e.g., core body temperature, skin temperature, etc.), and/or a determination of fever/no fever.

In some embodiments, the training dataset 382 includes data simulating real-time input to a virus surveillance system as described herein, and may include real data captured from an infrared, visible light, or other type of camera, and other sensor data captured from the environment. The data may also include synthetic data generated to simulate real-time sensor data. In one embodiment, the training starts with a forward pass through the neural network 380 including feature extraction, a plurality of convolution layers and pooling layers, a plurality of fully connected layers, and an output layer that includes the desired classification. Next, a backward pass through the neural network 380 may be used to update the CNN parameters in view of errors produced in the forward pass (e.g., misclassified data when compared to the label). In various embodiments, other training processes may be used in accordance with the present disclosure.

Figure 3D:
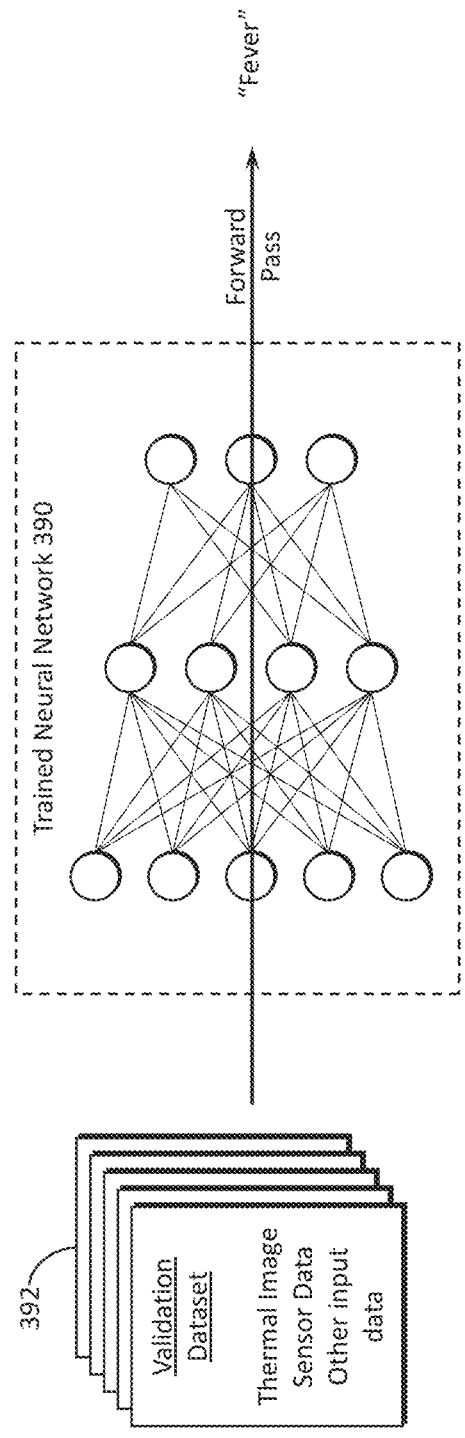
FIG. 3D illustrates an example virus detection validation process, in accordance with one or more embodiments of the present disclosure.

An embodiment for validating the trained neural network is illustrated in FIG. 3D. A set of fully annotated validation test data 392 representing real world data is fed into the trained neural network 390. The validation test data 393 includes a variety of thermal image data and sensor data to classify. Detected errors (e.g., image misclassification) may be analyzed and fed back to the training system to update the training model, which in turn updates the training dataset 382. In various embodiments, detected errors may be corrected by adding more examples of the data (e.g., more types of environments), increasing the resolution of the data and/or increasing the accuracy of the thermal modeling, to help distinguish between data types. By adjusting the training dataset to improve accuracy on-the-fly, the operator can avoid costly delays in implementing accurate virus detection surveillance systems.

In various embodiments, elevated body temperature detection systems are designed to operate with one or more trained CNNs. In some embodiments, measurement error is reduced, and the detected temperature is stabilized, by using CNN-based face tracking, a pan, tilt and zoom (PTZ) camera, a high resolution infrared camera with optical zoom, and/or other systems and methods for maintaining thermal image pixels on the face of the target (e.g., maintaining a number of pixels in a measurement area above a minimum threshold).

In some embodiments, a CNN is trained to identify an optimal measurement location within the captured pixels of a tracked person, which may depend on the areas of the skin and/or body that are available for measuring. The CNN locates an area that is determined to be the best available to the system for measurement accuracy, such as the target's forehead, tear ducts, and/or other locations.

In more general applications, such as hotel lobbies, restaurants, shopping malls, and other high traffic locations, a CNN is trained to determine the distance from the thermal camera to the tracked person, and automatically adjust the temperature measurement based on target distance from the camera. With people tracking across one or more camera fields-of-view, the system may be further configured to monitor a person's temperature as it changes over an extended period of time. In these embodiments, the system may track each identified person and maintain a quality of measurement metric on people. In some embodiments, the system is configured to identify measurement locations (e.g., eyes, skin), identify the number of pixels (or very that sufficient pixels) on a target measurement location, measure distance from camera, time on target, and/or other parameters. In some cases, an average crowd skin temperature can be determined from image determined be the parameters to be of high quality such that a temperature measurement is sufficiently reliable.

In many applications, the people being monitored are moving through the scene and the CNN is trained to identify times when the conditions are good for measurement, such as a face looking towards a camera, a face without glasses or a mask, etc. The CNN may also be used to identify people who do not comply with procedures for accurate measurements, such as people who have not, as instructed, taken off eyeglasses or hats. In some cases, the system may be configured to notify the target when the person has not provided a view with a sufficient measurement metric. For example, the system may include a laser, a directional sound or other indicia to encourage the target to look towards the thermal imaging system, allowing the thermal imaging system to capture thermal images for more accurate temperature measurement.

In various embodiments, the system is configured to store data generated in the field for further analysis and/or training of one or more neural networks. For example, data from a deployed system may be fed back into a CNN training process to refine the CNN for the particular environment (e.g., detect temperature of people in an airport, people attending a public sporting event, etc.), desired classification goal (e.g., train the CNN to detect temperature/symptom profile associated with certain infection) and/or for more accurate performance. In some jurisdictions, privacy regulations may prevent/limit data sharing for this use.

Figure 3E:
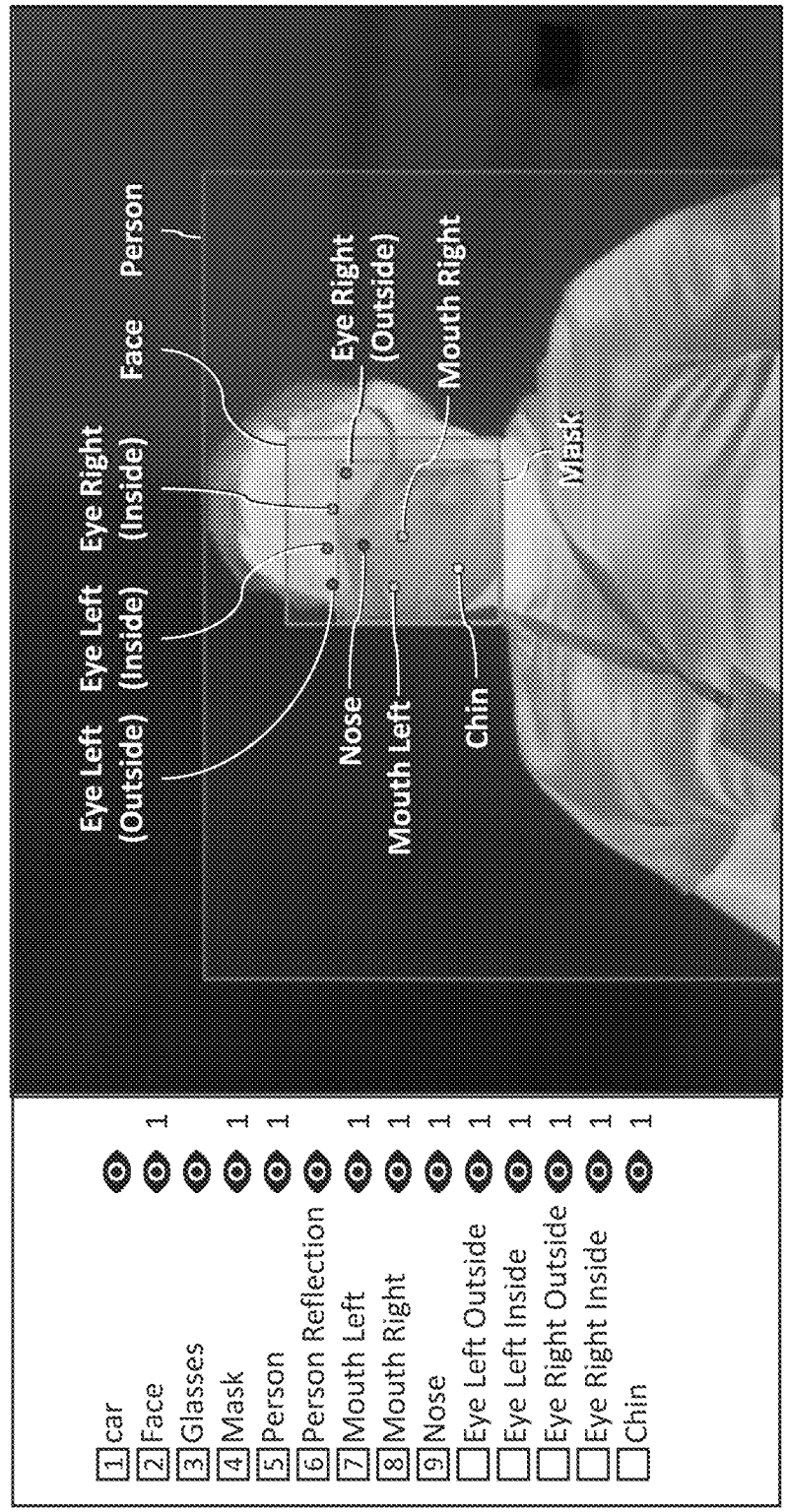
FIG. 3E illustrates an annotated training image, in accordance with one or more embodiments of the present disclosure.
Figure 3F:
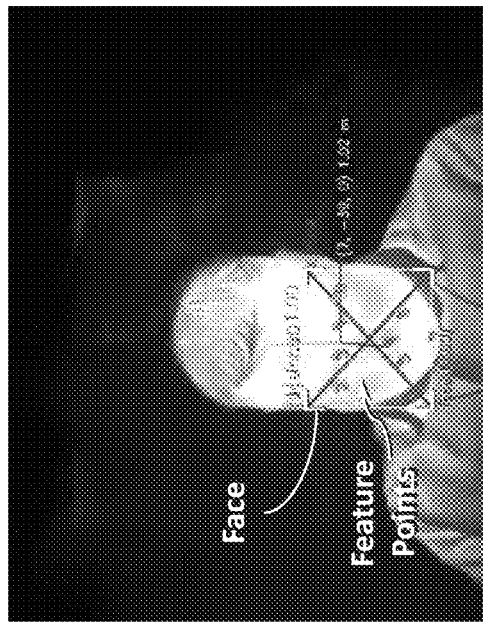
FIG. 3F illustrates example faces poses and annotated attributes for a training dataset, in accordance with one or more embodiments of the present disclosure.
Figure 3F:
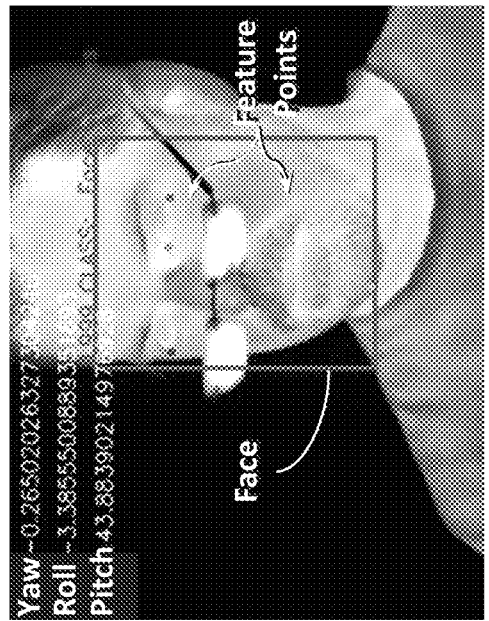
Figure 3F:
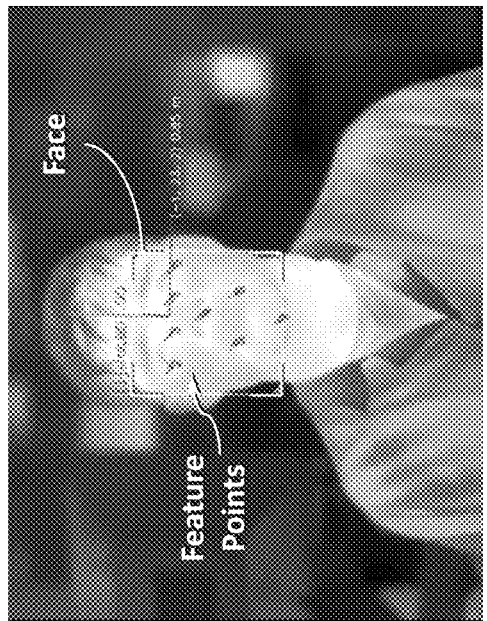
Figure 3F:
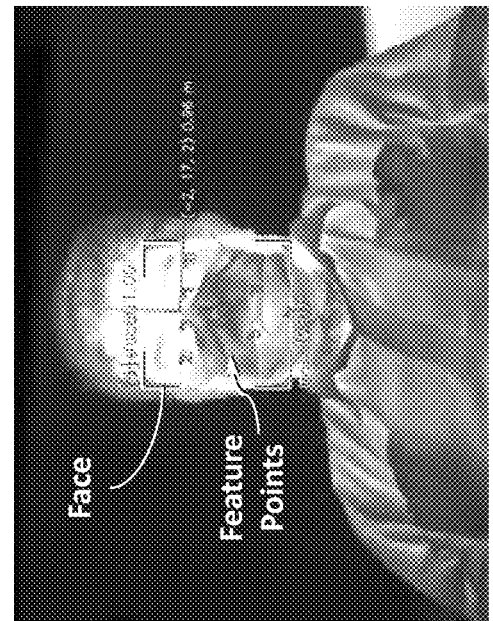
Figure 3G:
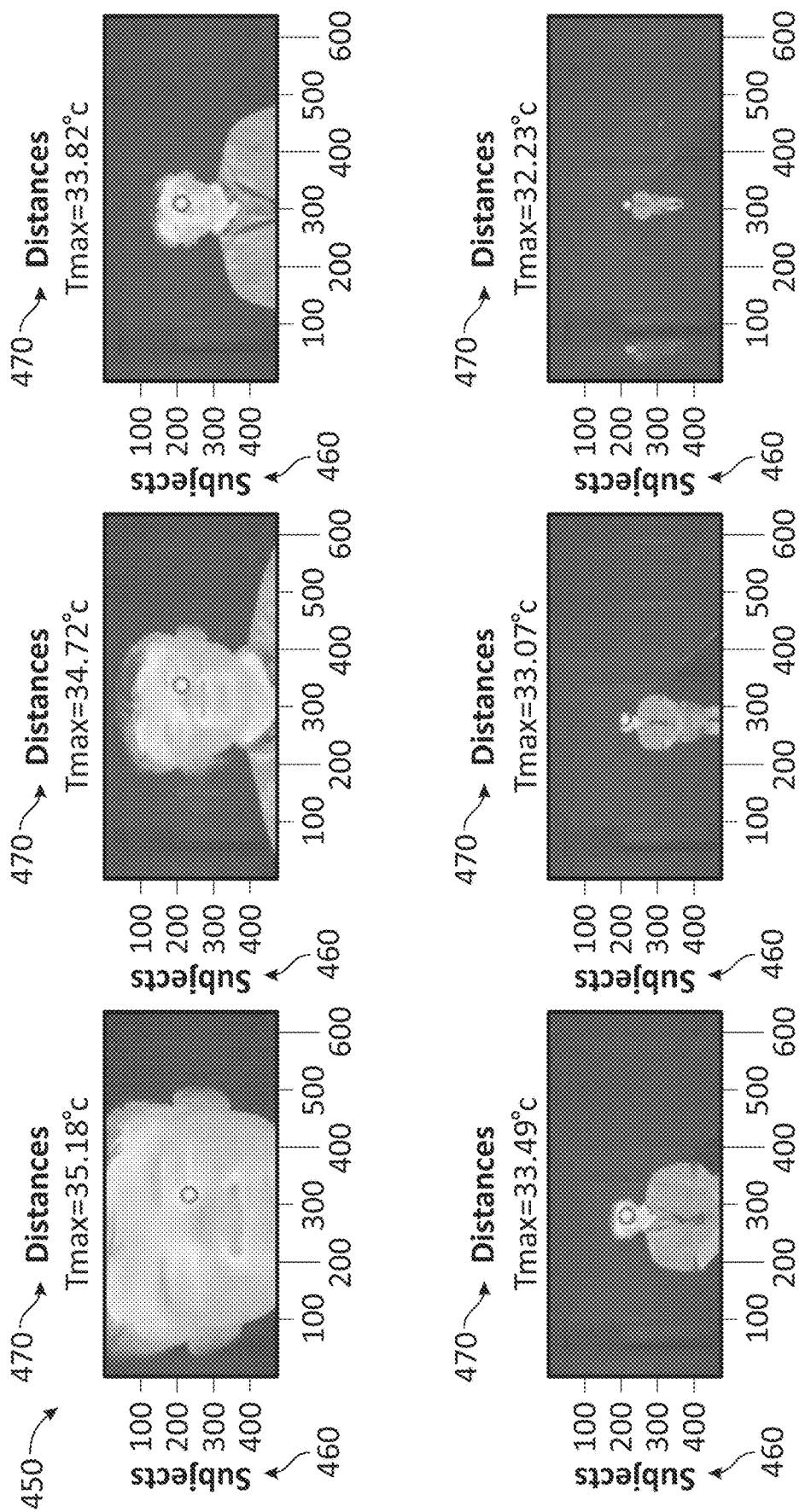
FIG. 3G illustrates example distance variations in a training dataset, in accordance with one or more embodiments of the present disclosure.
Figure 3G:
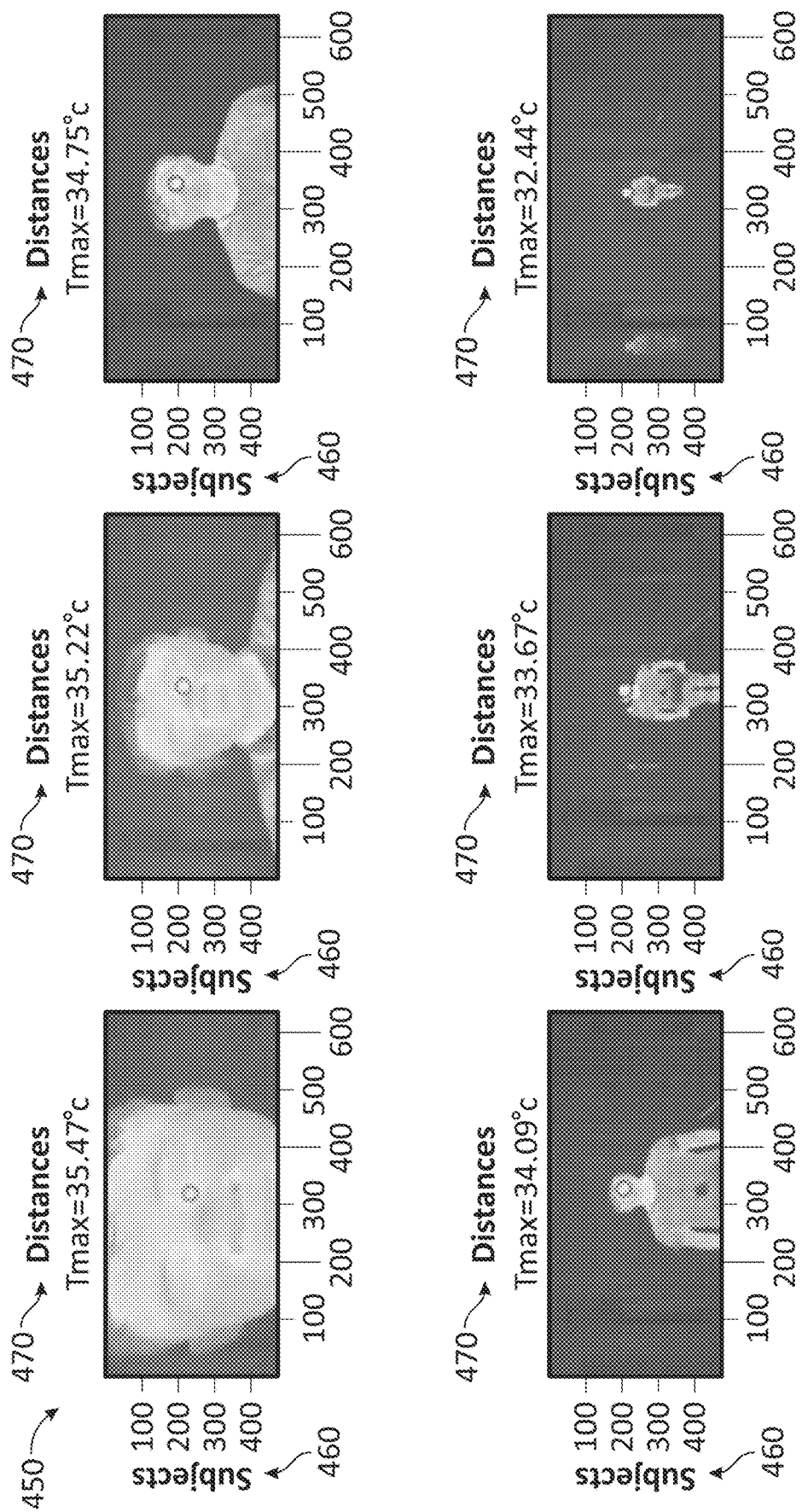
Figure 3G:
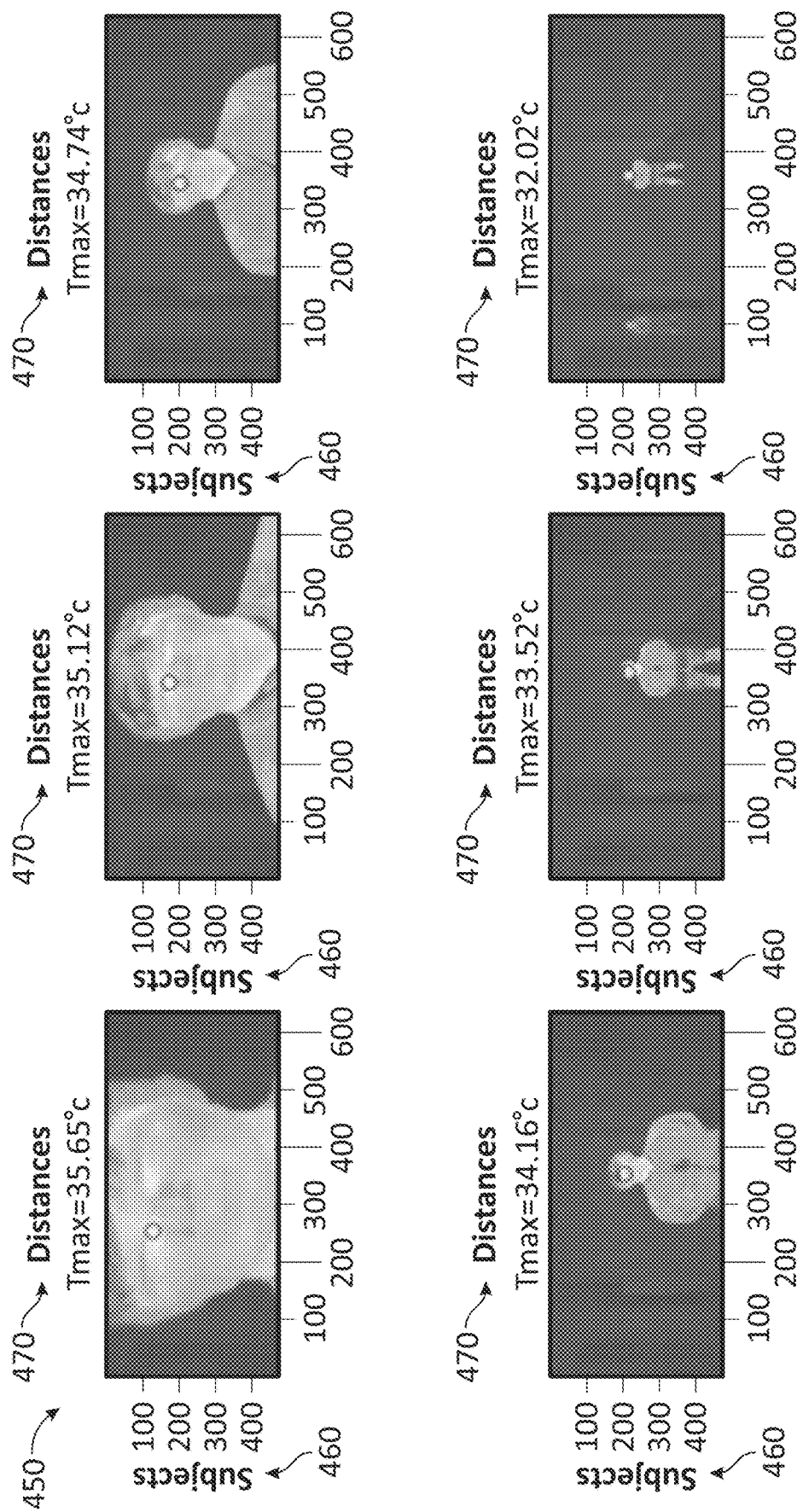
Figure 3G:
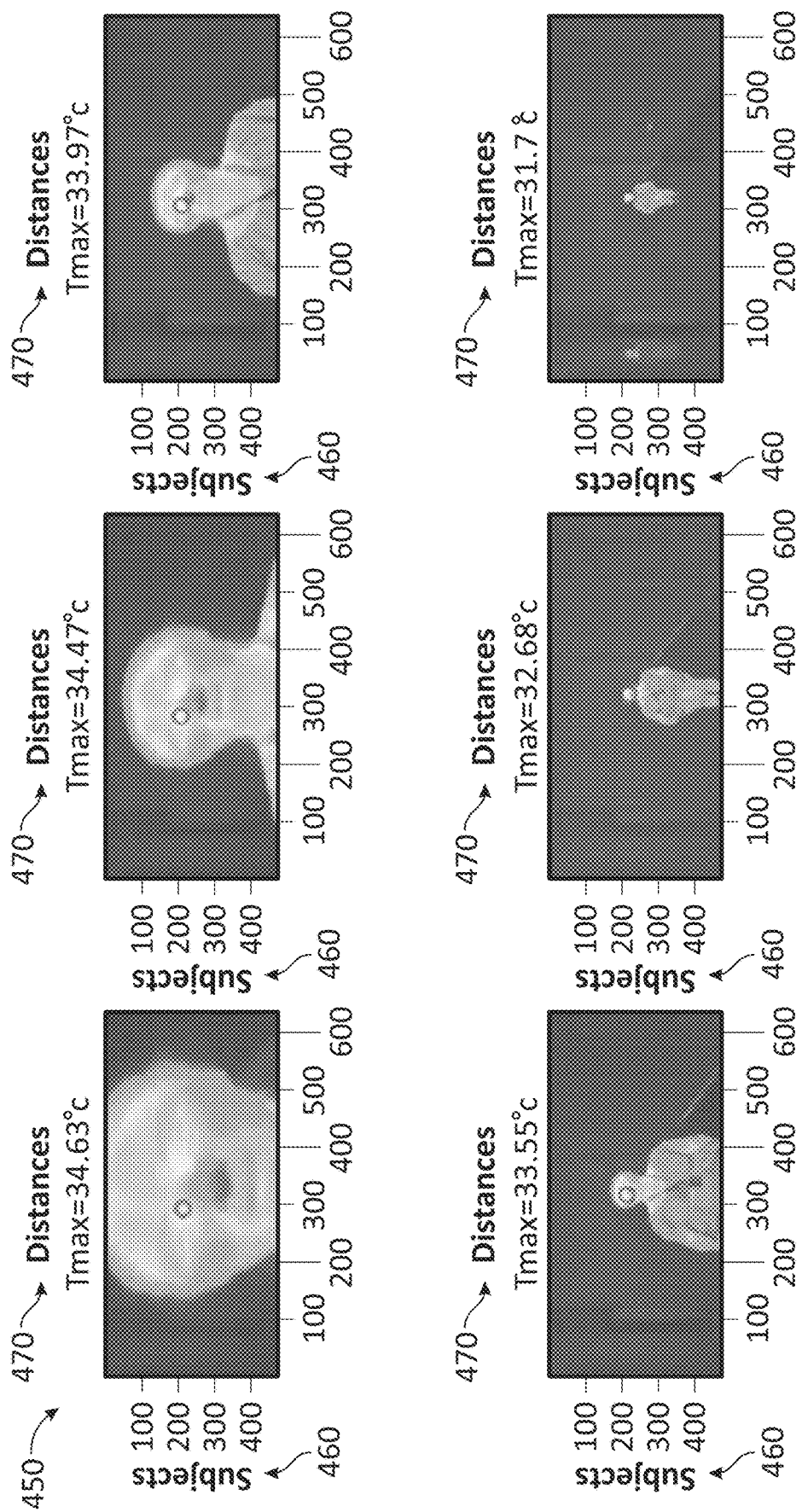
Figure 3G:
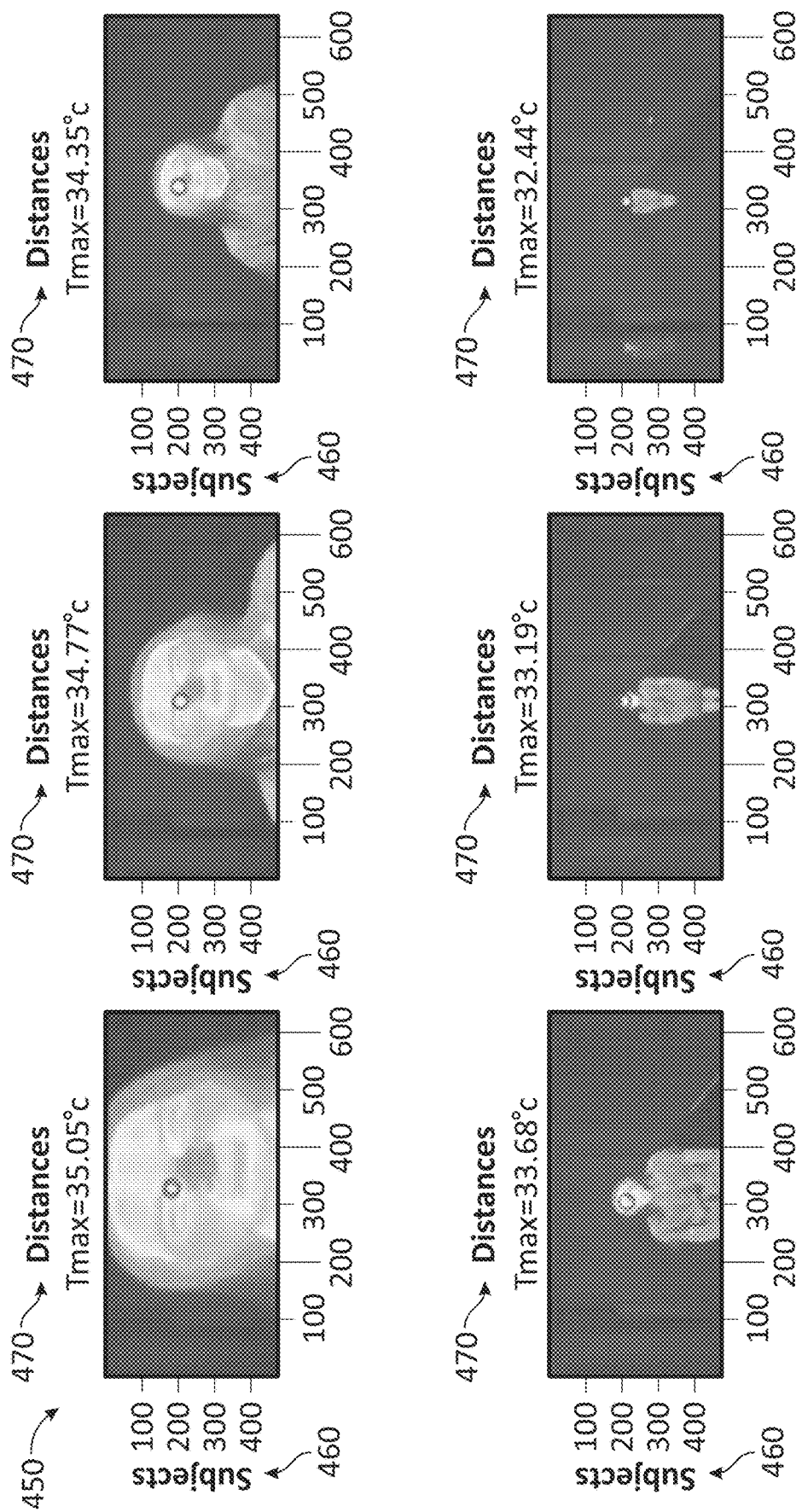
Figure 3G:
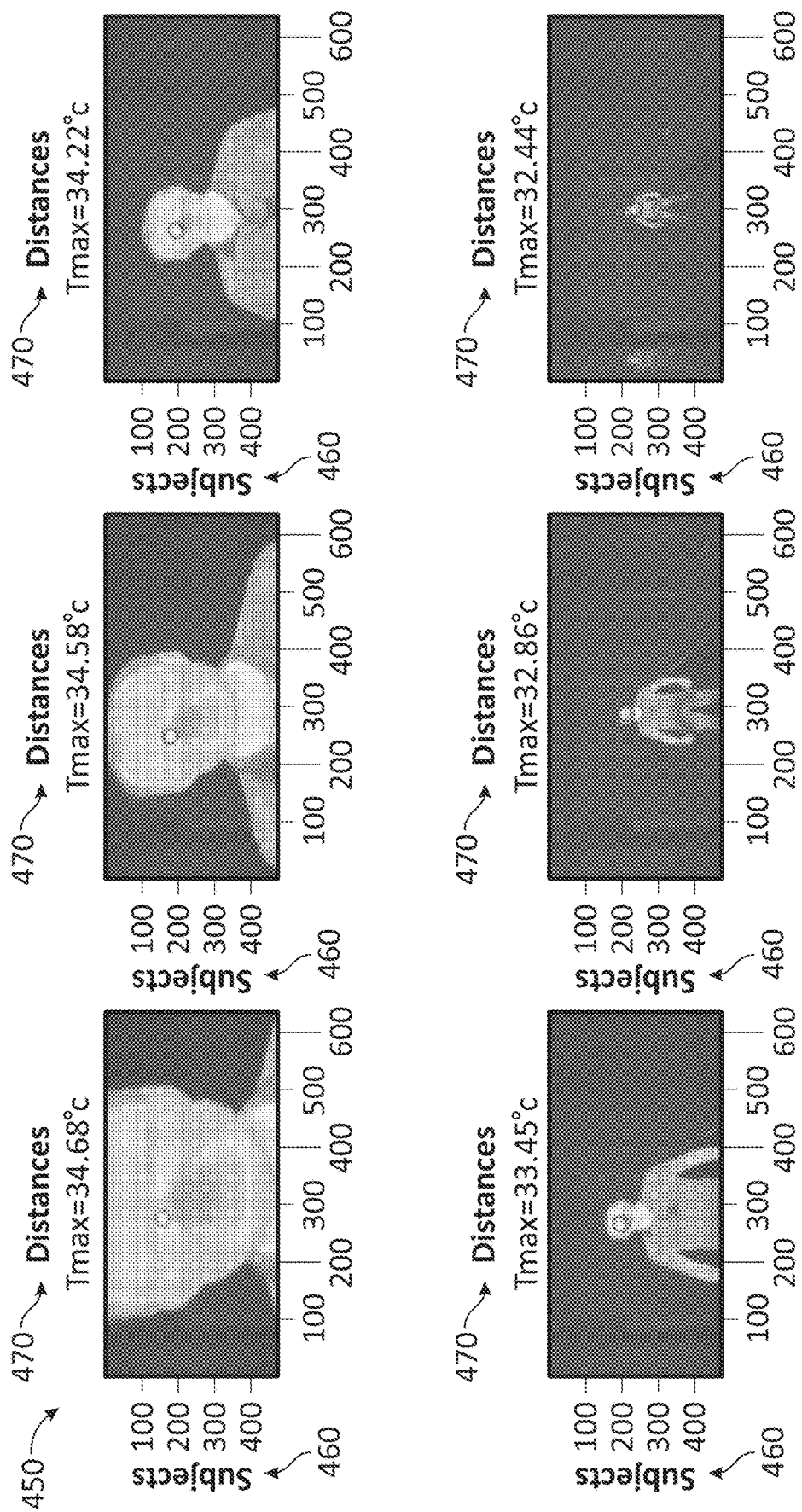

Referring to FIGS. 3E-G, further embodiments of CNN training systems and methods will now be described. As disclosed herein, screening temperature systems use one or more thermal cameras to measure persons to check if they are potentially in a febrile state. In some embodiments, face recognition is used to identify faces at different angles and/or distances and then find a desired location to measure the person's temperature. In many systems, for example, an accurate temperature measurement of the canthus is used for reliable results.

In various embodiments, CNNs trained on thermal data, combined with trackers, are used to provide a rich set of information, including face detection, face feature points (e.g., canthus), head pose, face attributes (e.g., glasses, masks, hat, etc.). This additional information is used to generate more accurate measurements and reduce system complexity. For example, the systems and methods of various embodiments use face detection to identify persons to measure. Face feature points are used to find the canthus, which is used for accurate elevated skin temperature measurements and fever screening. By tracking the head pose, the system can identify times when the person of interest is looking at the camera to validate the measurements. Head pose is used to validate measurements, by making sure the person of interest has properly "looked at the camera." Attributes such as masks and glasses are further used to validate the measurement and check for canthus occlusions. With use of pose and face detection, the system can additionally estimate the distance to target. In turn, elevated temperature systems can correct distance effects for greater temperature measurement accuracy.

Referring to FIG. 3E, a thermal training image 400 is annotated for face detection, including an identification of face feature points and attributes. For example, a thermal image 400 includes various annotations identifying head pose attributes, such as bounding boxes identifying locations in the image 400 of identified persons or objects such as a bounding box identifying a "person", a bounding box identifying a location of a "face" and a bounding box identifying a location of a "mask." Various face attributes identifying head pose information can also be included, such as annotations identifying locations in the image of the person's chin, sides of the person's mouth, nose, the inside and outside locations of the person's left eye and right eye, etc. The images may be gathered in the field, developed through test systems, synthetically generated, and/or gather from other methods. The annotations may be verified manually through a user interface 410 that includes a list of available annotations and associated location identifiers, such as a box, dot, graphic, icon or other identifier that may be placed on the image 400. The trained CNNs can be integrated into a tracker system for use in detecting elevated skin and/or body temperature.

In some embodiments, one or more CNNs are trained to provide face detections. By identifying the faces in an elevated skin temperature system, the system is configured to make sure to only measure when a person is present in the thermal imagery. This helps reduce false positives due to other hot objects (hot cups) in the scene that have similar temperature as a febrile person. Additionally, this helps with measurement consistency, people counting, multi people measurements, and temperature measurement in scenarios that do not requiring stationary subjects.

The one or more CNNs provides localization of various feature points on the face (e.g., as illustrated in FIG. 3E)). In some embodiments, those feature points are used to identify a measurement location, such as the canthus on the face. The canthus is an area on the face that correlates with the person's core body temperature and in turn whether a person is febrile or not. Using the canthus feature points, a maximum temperature region of interested is identified and used for temperature measurement. An elevated temperature system may then use that measurement to determine if the person is febrile or not per system decision rules. Additional benefits of feature points as described herein include, but are not limited to, not requiring stationary subjects, and reducing measurement variance/false positives due to potential hot spots on a person faces (hot summer day for example).

The CNN, combined with the feature tracker, can be used to provide head pose information. Referring to FIG. 3F, image 420 illustrates a face identified with feature points (e.g., corresponding to feature points of FIG. 3E). The system captures images of a scene and processes the image through the trained CNN to identify the location of the face and each of the tracked feature if visible. The system checks whether the person being tracked has looked at the camera based at least in part on the relative locations of the feature points with respect to the camera. For example, image 422 illustrates a captured image of a face looking downward, and image 424 illustrates a face looking towards the camera. In various embodiments, the position of the head is measured and compared to a certain pitch, yawn, and roll thresholds to determine image capture times in which the head is positioned for an accurate temperature measurement. If the person is looking away (e.g., image 422), the system can mark the measurement as invalid. If the person is looking directly to the camera within the threshold (e.g., image 424), the system can mark a corresponding temperature measurement as valid. In some embodiments, this approach may be used to automatically cue the person to look at the camera properly, avoiding situations where the canthus is occluded due to head pose. For example, based on the calculated pitch, roll and/or yaw, the system may cue the person to adjust his/head towards the camera. Additionally, there is the possibility of applying an angular correction to the measurement for better absolute accuracy.

In various embodiments, the CNN provides attributes, such as masks/no-mask, glasses, canthus occlusion, etc. Canthus occlusion/glasses is used to invalidate measurements and cue the person to remove the occlusion (example glasses). Masks/no-masks have potential to be used to correct for temperature measurement, as a potential source of measurement temperature variance may be due to masks. Additionally, it can be used to validate if a person entering a building is wearing the required PPE.

Combining the above information, a tracking system estimates the distance from the camera to the subject. In some embodiments, the training data includes training images of subjects at varying distances, such as illustrated in FIG. 3G which depicts images 450 for a plurality subjects 460 and a plurality of distances 470. The subjects 460 may each have a temperature that is measured at different distances 470 from the camera, resulting in different measured temperatures, which are then adjusted based on the distance. In various embodiments, a CNN may be trained to determine distance from the camera to the subject, and/or the distance may be determined using known properties of the camera and system configuration and knowledge of the scene (e.g., a distance to a monitored entryway).

Figure 3H:
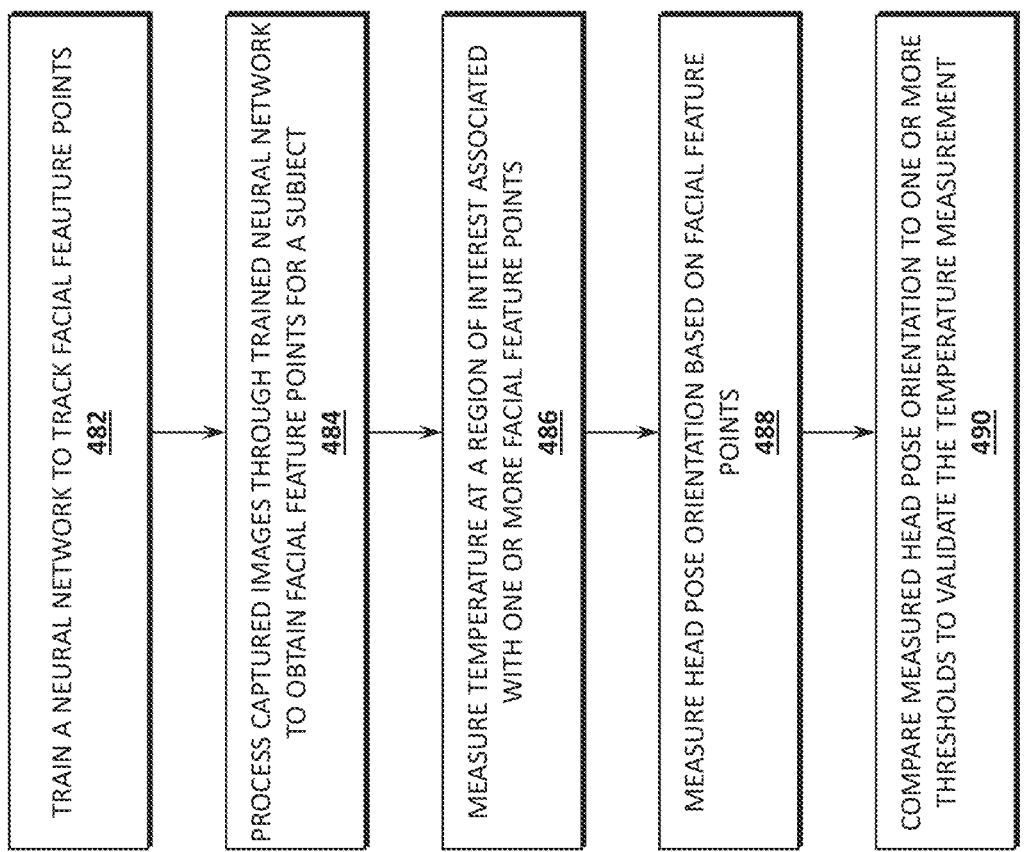
FIG. 3H, illustrates an example process for detecting elevated temperature of a subject, in accordance with one or more embodiments.

Referring to FIG. 3H, an example process 480 for detecting elevated temperature of a subject will now be described, in accordance with one or more embodiments. In step 482, a neural network is trained to track facial feature points, for example, as described above with respect to FIGS. 3A to 3G. In various embodiments, the facial features may include bounding boxes identifying subjects (e.g., one or more persons), bounding boxes identifying facial features or objects (e.g., a face, a mask, etc.), and a location of a plurality of facial features (e.g., chin, eyes, nose, mouth, etc.). In step 484, a trained neural network is used to process captured images of a scene to identify subjects and facial features. In step 486, the system measures a temperature at a region of interest associated with one or more facial feature points (e.g., an eye canthus), which may include an estimated distance to the person's face, which enables a potential correction of the temperature measurement of the canthus. In step 488, the system measures a head pose orientation based on the detected facial feature points. In some embodiments, the system assumes a nominal three-dimensional face model and matches it to the features points and pose, and measures a yaw, roll, and/or pitch to determine whether the subject is facing the camera. In step 490, the system compares the measured head pose orientation to one or more thresholds to validate the temperature measurement.

If the head pose orientation is within the one or more thresholds, then the temperature is validated. Otherwise, the temperature measurement may be discarded. Additionally, the system may validate temperatures measurements by checking if a person was too far or too close to a camera and may adjust a temperature measurement based on the estimated distance and/or head pose orientation. By using CNNs on thermal imagery instead of visible imagery, the elevated temperature system does not need to correct for parallax issues in trying to localize the canthus in visible and transferring that location to the thermal, thus measurement variance is decreased.

Elevated Body Temperature Systems and Methods

Various embodiments for improving one or more aspects of elevated body temperature systems and methods will now be described in further detailed with reference to the remaining figures.

1. Systems and Methods for Improved Measurement Stability

Figures 4, 5A:
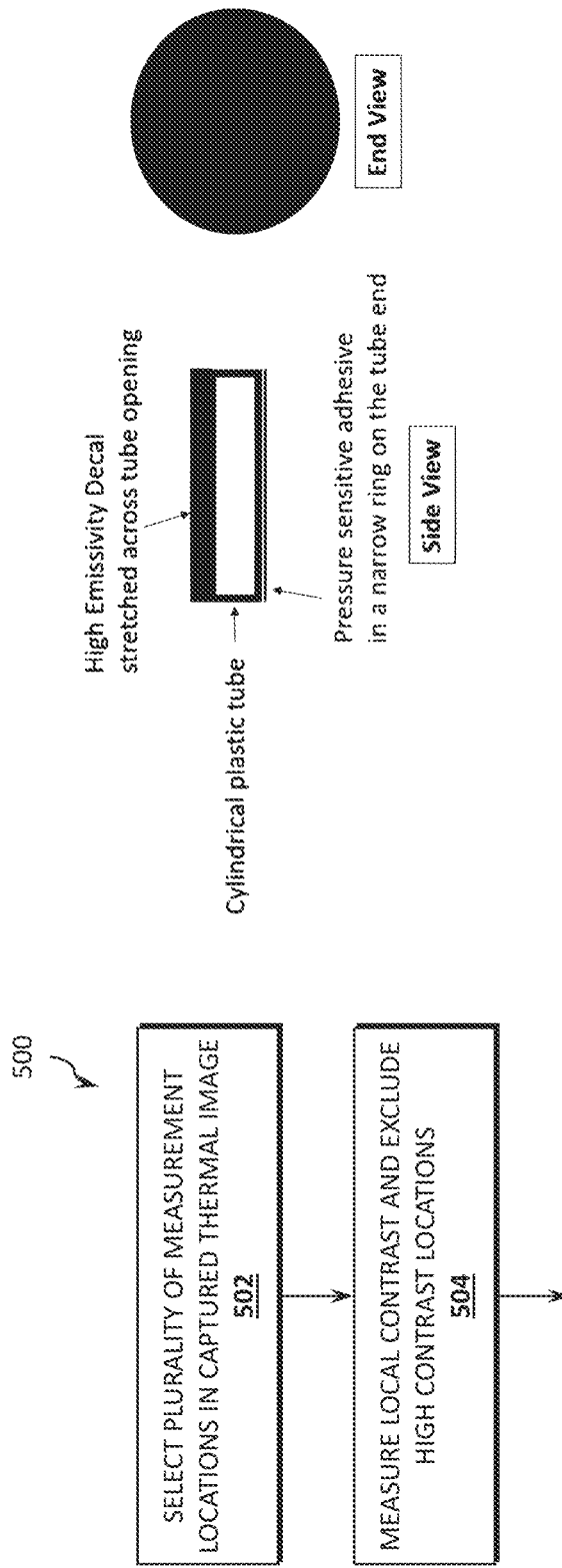
FIG. 4 is a flow chart illustrating an example process using scene information as a black body, in accordance with one or more embodiments of the present disclosure.
FIG. 5A illustrates an example black body decal that may be used in the process of FIG. 4, in accordance with one or more embodiments of the present disclosure.

In one or more embodiments, improved measurement stability may be achieved by using the scene (e.g., scene 170 of FIG. 1B) as a "black body." Referring to FIG. 4, a process may include selecting a number of random or predetermined measurement locations within the captured thermal image of the scene, in step 502. Next, local contrast is measured, while excluding points with high contrast (e.g., pixels that may indicate strong edges), in step 504. High contrast points may be determined, for example, by comparing the contrast of neighboring pixels and excluding measurement locations where the contrast exceeds a threshold contrast value. In some embodiments, the number of pixels N that are selected may be kept constant by selecting a new location for every location that is excluded such that we have a minimal set of low spatial contrast points in the scene identified.

The signal at each of the N points is then measured over time, in step 506. For example, the measurement may be taken at a regular time interval T and the collected values may be stored in a memory. Next, points that have a significant signal variation over time (e.g., having a standard deviation of the signal that is over a threshold) are excluded from the set of points used to improve stability, in step 508. In some embodiments, the number of locations N may be kept constant by selecting a new location for every location that is excluded such that a minimal set of low temporal variation points in the scene is identified.

The system then monitors and compensates for drift in the measurements, in step 510. In some embodiments, the mean or median of the N stable points is calculated to monitor drift in the measurement. For example, high temporal frequency drift can be eliminated out by subtracting a highly damped aggregate value of the N samples from the sampled signal values in the image. The aggregate value can be mean/median or other weighted combination of the used samples. Stability in space and time can be constantly monitored to take out outliers or pixel samples that are frequently occluded by for example people passing through the scene. Slow temporal drift can be allowed to compensate for temperature changes in the overall scene.

In some embodiments, a black decal that sticks onto a surface in the scene that is at ambient temperature may be used. The black decal location could be used as one of the predetermined measurement locations mentioned above. The surface that the decal is attached to should not be one that is subject to significant heating from anything other than ambient air temperature. As illustrated in FIG. 5A, the decal may have a high in-band emissivity for the camera being used, e.g., it could be something like Acktar Black. The decal serves as a reference point in the scene for ambient temperature. One drawback of the decal being applied to a surface that has a high thermal conductivity is that the decal may not track air temperature changes the way that a thermal camera/lens combination would. One solution to this could be to use a spacer ring under the decal so that the decal has an air void underneath it. This is similar to a microbolometer element, or the sensors on a rattlesnake and pit viper where a thin membrane is stretched across an opening in the snake's face to reduce its thermal contact with the snake. The decal would then have a lower effective thermal mass and would track air temperatures with a thermal time constant that is closer to the time constant of a thermal camera/lens combination. It might also be possible to tailor the time constant of the decal by applying it to an aluminum disc. The thicker the disc, the higher the time constant, which can be determined experimentally. The decal stuck directly to a surface in the scene is likely to have a different time constant, depending on the thermal conductivity of what it is stuck to.

In some embodiments, additional stability can be achieved using an image processing algorithm to separate the background from the people. This may be performed through various techniques, including image analysis or spatial analysis to identify objects in three-dimensional space, by identifying and removing a learned background, etc. The background can be used to stabilize the signal over a shorter time, particularly if manual calibration is needed on a regular basis.

Figure 5B:
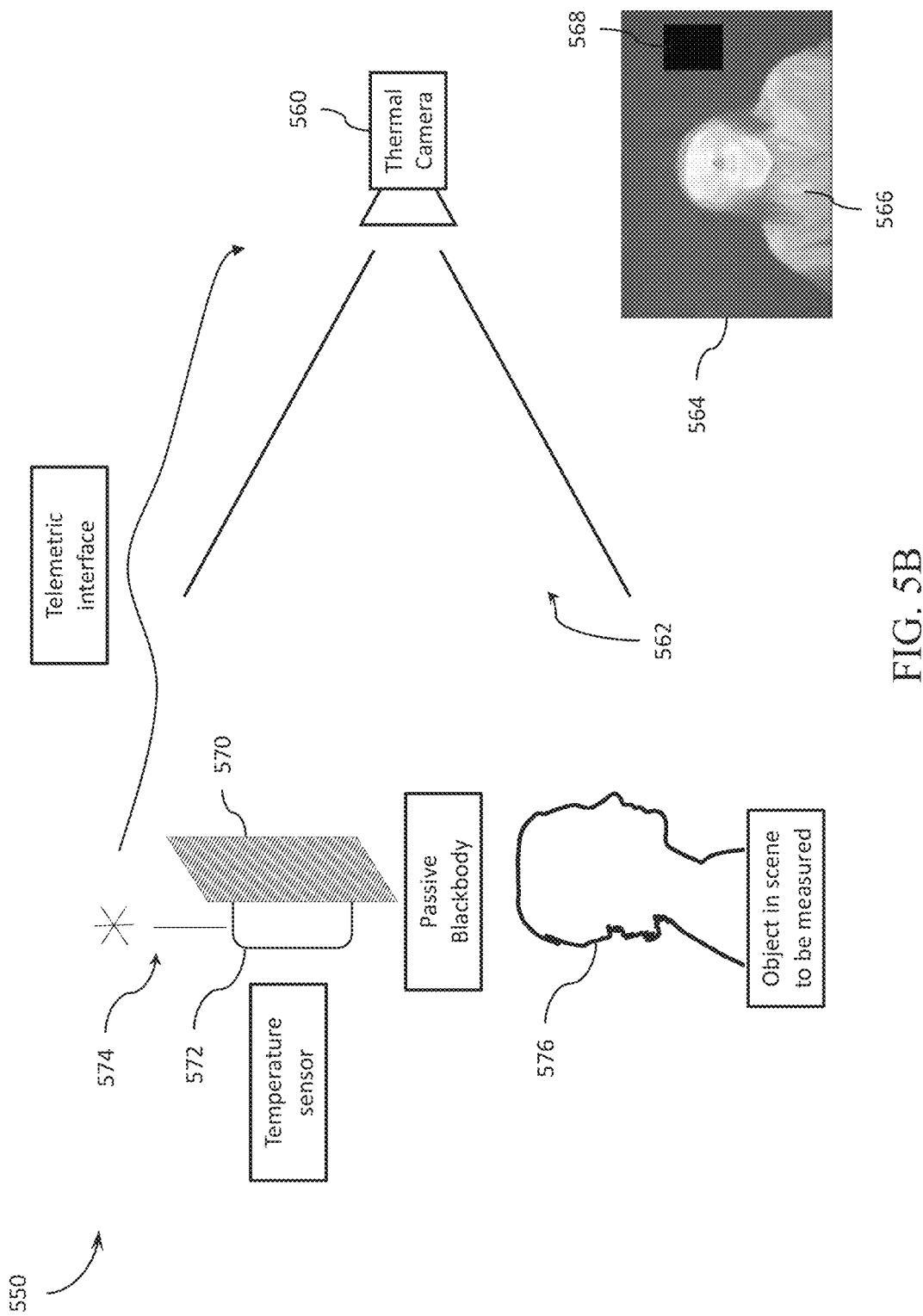
FIG. 5B illustrates an example passive black body and telemetry system, in accordance with one or more embodiments of the present disclosure.

Referring to FIG. 5B, an example black body is described in accordance with one or more embodiments that may be used to increase the radiometric accuracy of a thermal imager at low system cost and complexity. A system 550 includes a thermal camera 560 configured to capture thermal images (e.g., thermal image 564 including an object 566 and an image of a black body 568) of a scene 562. The scene 562 includes a passive blackbody 570 in view of the thermal camera 560. In various embodiments, the passive blackbody includes a low-cost passive blackbody for use as an in-scene radiometric reference. A temperature sensor 572 senses the ambient temperature at the blackbody and includes a wireless interface 574 for transmitting the sensor information to the thermal camera 560 over a telemetric interface.

In this system 550, the accuracy of remote temperature measurement using the thermal imaging camera 560 is improved because the system 550 provide an accurate reference temperature for the blackbody 570. The thermal camera 560 captures the thermal image 564 of the scene, which includes an image 568 of the blackbody 570 and uses that portion of the thermal image to provide an accurate reference that relates pixels to temperature. This system is effective and doesn't require a costly active blackbody and/or knowledge of the actual blackbody temperature (which can vary, e.g., due to warm-up time and the effect of the environment on the actual blackbody temperature). The illustrated embodiment replaces an active blackbody of conventional systems with a passive, unpowered blackbody that uses an electronic or other method to provide a high-accuracy measurement of the blackbody's temperature and then relays this temperature using a telemetric interface (e.g., Bluetooth) to relay the blackbody's temperature in real time to the radiometric thermal imaging sensor.

In one embodiment, the passive blackbody 570 includes an aluminum plate with a high-emissivity coating. The temperature sensor is one or more low-power high-accuracy solid state temperature sensors with digital output in thermal contact with the viewed surface. The connection to the thermal camera 560 is a low-power wireless link (e.g., Bluetooth) over which the blackbody temperature is relayed. The temperature sensor 572 and wireless interface could operate for long periods of time, e.g., using a lithium coin cell and/or operate using solar power or other low power approach.

In some embodiments, the system 550 could also include collapsible bellows that shield the blackbody from air currents that might cause the temperature to fluctuate or vary over the surface. The same bellows could be used to make the blackbody self-standing in the scene, for example.

2. Use of Motion Statistics of Measurement Points for Human Classification

One challenge in fever monitoring systems is to correctly identify points in a captured image as being part of a person's face. The present disclosure describes improved thermal imaging systems with built in analytics capable of correctly classifying a sampled data point as being part of a face. The methods described herein provide more efficient and accurate face detection than conventional face detection algorithms.

Knowing that the collected temperature value is from a face is important to many systems so that it can automatically update the population mean/median statistics to determine if a person has an above normal skin temperature. Collecting the mean/median is currently a manual process requiring user interaction and it is prone to mistakes. User fatigue may also prevent the population statistics from being updated and an automated collection is desired.

In one or more embodiments, the trajectory of the sampled max values is analyzed. People moving through a scene will typically follow on a few possible motion paths. They are either walking towards the camera or passing through the FoV along some path determined by the physical layout of the scene and the mounting position of the camera. The thermal cameras can detect the max temperature in the scene or in some region of interest (ROI) within the scene. If the person is moving and the person's face has an apparent temperature that is higher than the background the location of the highest "temperature" pixel will follow a recognizable path in the pixel XY plane. For example, if no person is present the max may be very still and may have a value that is lower than typical value as measured on the skin in the face of a human. If the max value location is "jumping" from one location to another location in an erratic pattern this may also be an indication that the max measurement does not belong to the face of a single human in motion. These values may also be excluded from the population statistics collection.

Figure 6:
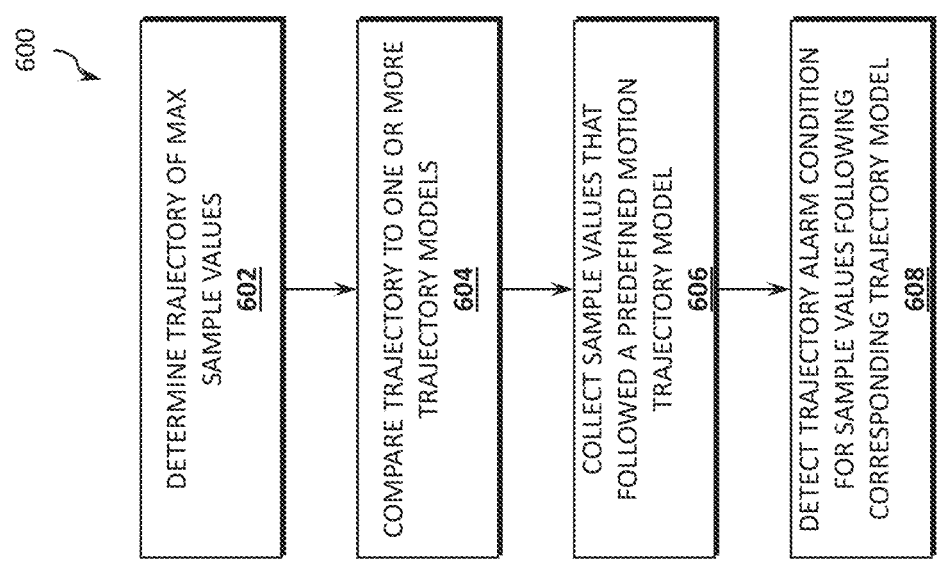
FIG. 6 is a flow chart illustrating an example process for identifying pixels on person's face, in accordance with one or more embodiments of the present disclosure.

Referring to FIG. 6, an example process 600 for identifying samples to track and measure will not be described, in accordance with one or more embodiments. First, the system determines a trajectory of maximum sample values, in step 602. Next, in step 604, the system compares the trajectory to one or more trajectory models. In step 606, the system collects sample values that followed a predefined motion trajectory model. For example, the system may specify that only sampled values that follow a predefined motion trajectory model are collected. In this manner, people are excluded that are coming from a different location in the scene where they have been exposed to a different environmental threshold and therefore can be expected to have a different skin temperature than the group the system is designed to monitor at this location.

Alternatively, two or more motion trajectories can be defined, and separate statistics can be collected for those groups. This could be for example people entering or exiting an area. This allows the system two have two (or more) separate sets of alarm levels depending on the trajectory of the sample. In step 608, the system detects an alarm condition for sample values following the corresponding trajectory model.

Figure 7:
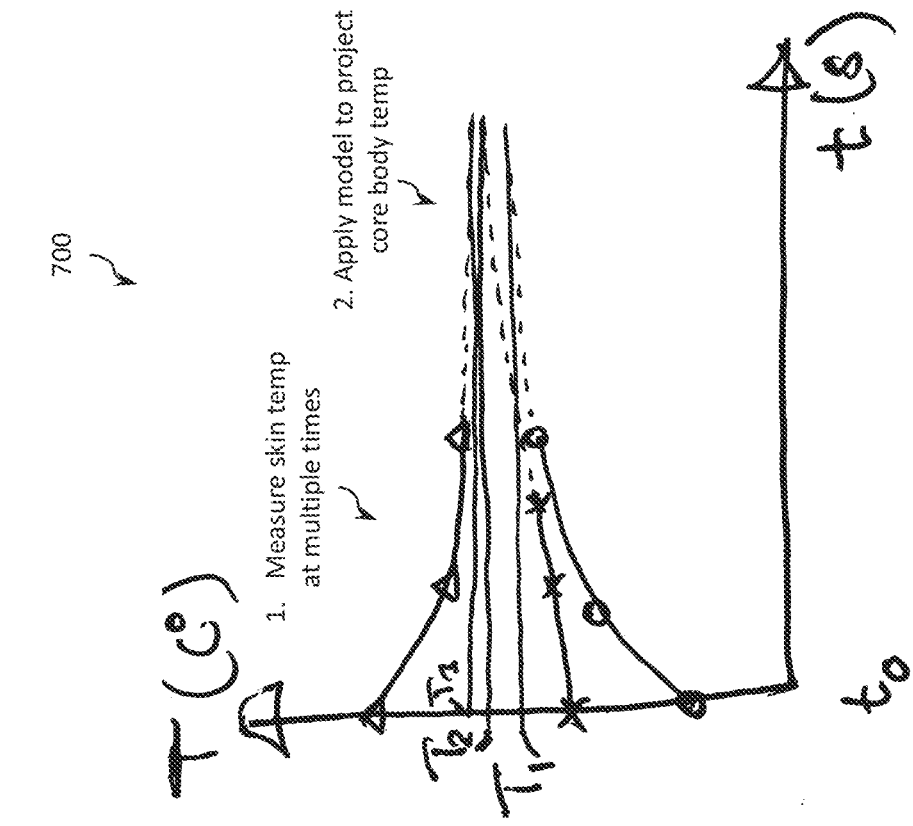
FIG. 7 is a chart illustrating temperature measurements over time, in accordance with one or more embodiments.

3. Estimation of Actual Core Body Temperature Using Multiple Measurements Over Time Embodiments for estimating actual core body temperature will now be described with reference to the chart in FIG. 7. It is well known that a person coming from the cold outside air and a person coming from a warm car will have very different skin temperature even if their core body temperature is similar. It is expected that this difference is reduced over time as persons are exposed to the same environment (e.g., waiting inside an airport or train station). By tracking the same individual (for example through a tracking algorithm or through image-based identification and re-identification) a surveillance system can monitor the temperature of the skin in the face of an individual over time.

By measuring the rate of change of the skin temperature over time, the system can estimate the "steady state" asymptotic value the person will eventually reach. This allows the system to compare people coming from different environments and will reduce the number of false negatives for people coming from a cooler environment and false positives for people coming from a warmer environment. The samples gathered over time may be from the same thermal imager (for example if people are in a queue and therefore are present in the FoV for a long time) or the samples may come from different thermal imagers in different locations along the movement path of the people being monitored. For example, a person may be tracked at an entrance of an airport and later as the person is trying to check in or go through security.

The chart 700 illustrates that a large temperature difference at the time of first sampling of a human can be reduced to a very small difference if the system extrapolates to a future time. For example, the system may model a rate of change in the face temperature as it adjusts to the new environment which may then be used with minimal samples (e.g., only two samples) with some known time between them to estimate the "true" core body temperature or the "true" face temperature.

4. Monitoring System Drift Using Stereo Thermal System

Figure 8:
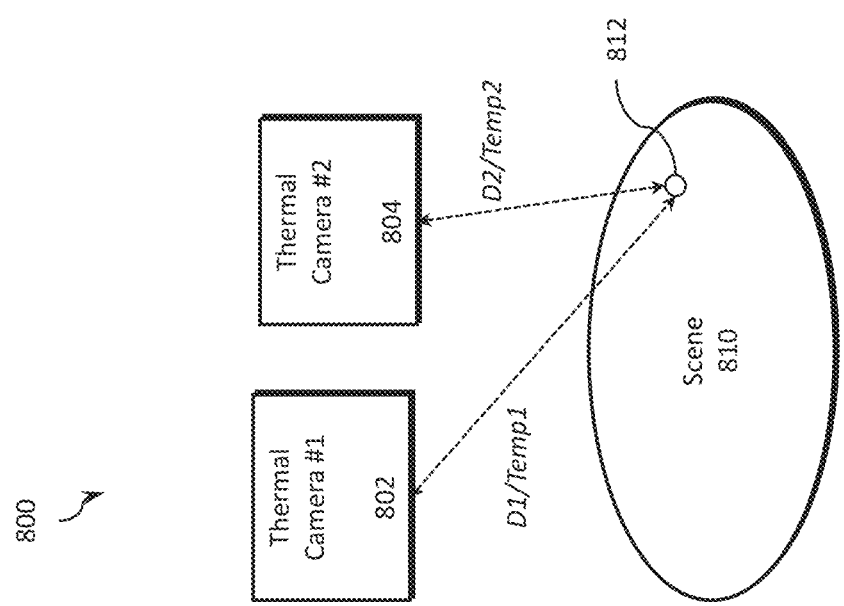
FIG. 8 illustrates an example stereo thermal system including drift monitoring, in accordance with one or more embodiments of the present disclosure.

Referring to FIG. 8, an example method for monitoring system drift for recalibration will be described, in accordance with one or more embodiments. A system 800 includes at least two thermal cameras, thermal camera #1 802 and thermal camera #2 804 providing stereo thermal (e.g., for creating a depth map). Separate temperature measurements Temp1 and Temp2 are taken of a point 812 in a scene 810. Because there is a distance dependence on the temperature measurements, the temperature measurements are distance adjusted (e.g., using distance D1 to adjust Temp1 and distance D2 to adjust Temp2) and compared. If the two values are within an acceptable error threshold, then the measurement is accepted. If the adjusted measurements are outside the error threshold, the system can be "flagged" as needing recalibration, or service, and the measurement may be flagged as having error.

5. Focused Deployment at Existing Crowd Flow Choke Points

Figure 9:
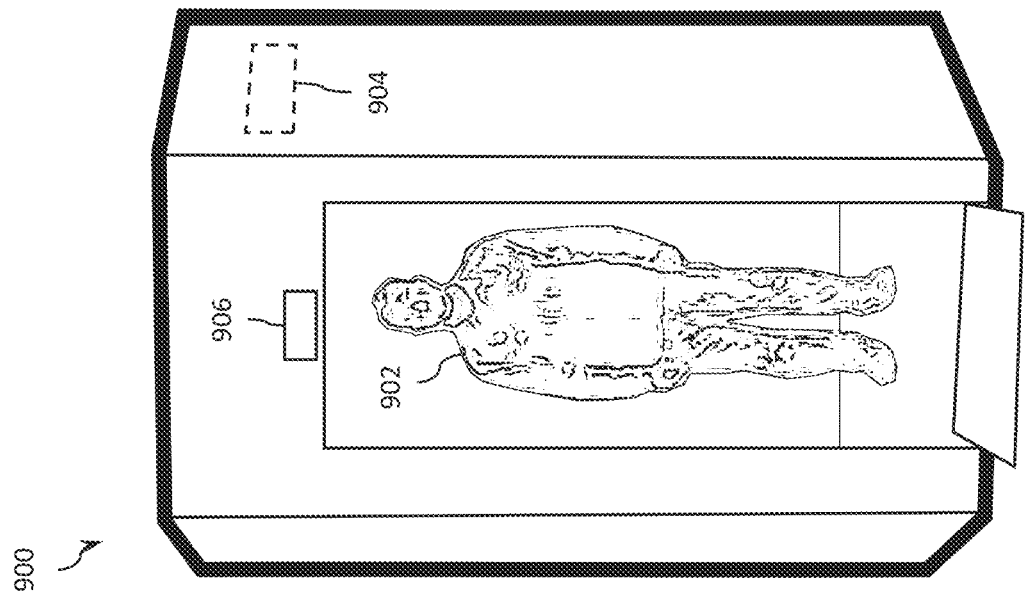
FIG. 9 illustrates an example airport millimeter wave scanner, in accordance with one or more embodiments of the present disclosure.

Referring to FIG. 9, an example airport millimeter wave scanner with virus detection will now be described, in accordance with one or more embodiments of the present disclosure. The addition of a thermal imager to currently existing millimeter wave scan portals, such as millimeter wave scanner 900 would allow for focused measurement of a targets face with known or measurable distance to target. The typical 'hands above head, palms outward" stance required for millimeter wave scans presents the ability to capture targets in a known orientation for easy focus/capture of face/eye area (or other areas of interest: inside of wrist, armpit, throat—which could be used as either reference or indicator measurements). The cameras, such as thermal camera 904 could be added as attachments or integrated in the scanner.

In some embodiments, a thermal camera 906 can be placed at an entrance/exit of the scanner 900 (e.g., on or near an exterior of the scanner) to capture a thermal image of a person 902 from a known distance as the person enters/exits the scanner. A black body or 'black decal' (as presented above) in camera FOV may also be used for continuous calibration. Most thermal transients associated with high/low outside temperatures will have normalized by the time a target reaches point of scan, which allows for more accurate temperature measurement.

By deployment the thermal cameras at existing choke points, temperature scanning will not impact crowd flow as the thermal image can be captured and assessed in parallel to the millimeter wave scan. Additional thermal cameras could be deployed at other known points as well such as bag check/check in kiosks or TSA ID/Passport verification point.

6. Use of Low-Cost Powered Blackbody to Correct for Camera Drift

A thermal camera that is not radiometrically calibrated can be used to monitor relative surface temperatures in a scene if the camera digital data can be drift-corrected by the use of a powered blackbody source in the scene. The blackbody runs at a constant temperature which would be something close to 38 C, or the temperature of someone's forehead if they are febrile. The blackbody source has a high emissivity so that it acts as a stable radiance source with very low reflectivity. The source can be relatively small, in this case about 1 inch by 0.5 inches in size. The requirement that a target should be at least 10 by 10 pixels apparent size in the image for accurate temperature measurement is relaxed here, since we don't have to measure absolute temperature, we only need a stable radiance source. Because the blackbody is running at a temperature that is elevated from ambient, it only has to be heated—there is no need for a TE cooler. A low-cost powered blackbody could consist of a wirewound power resistor that is thermally bonded to a heat-spreading plate made of aluminum with a high emissivity black coating on the viewable side. A wirewound resistor in a metal or ceramic case is relatively inexpensive and the cases have flat surfaces on them which makes it easy to attach them to another flat surface, in this case, the heat spreading plate. The heat-spreading plate could have a thermistor attached to it close to the resistor case. A very simple electronic circuit monitors the resistance of the thermistor and adjusts the drive current to the resistor using a power transistor circuit. The blackbody will run at a temperature that is controlled to be very stable in ambient temperature conditions. It is not necessary to have the blackbody running at a precise temperature value, only that it be stable. Air currents are kept off the viewable surface by using a cowling around the front of the blackbody to improve temperature stability. By not requiring an absolute temperature precision, the need for calibration is removed which saves cost due to reduced complexity of the circuitry and the reduced need for touch labor. The thermistors used for the temperature control are inexpensive and have fractions of a degree C. interchangeability, so these sources should all be within plus/minus 0.5° C. of each other anyways.

In some embodiments, a design for a powered blackbody would be a 5 mm coated aluminum plate heated with a film heater. This would have the advantage of being larger and more uniform than the wirewound resistor concept. The heater would be manufactured to have a thermistor epoxied to the back, and that thermistor could be read out by a control circuit which would also be able to communicate its temperature to a camera system via Bluetooth or another interface. The aluminum plate could have a black decal applied to it which has a very high emissivity. This reduces the touch labor that painting requires. The heater would be controlled by a PID controller with an adjustable setpoint that would be set via Bluetooth from an app, or perhaps via a micro-USB cable from a host PC. In one embodiment, a blackbody enclosure design is a plastic sphere with a hole in the side. The camera looks into the hole and views the plate which is recessed 1 inch inside the sphere. The sphere is on a pivoting mount so that the hole can be lined up on the camera. The recessed design makes the blackbody emitter surface much less susceptible to air currents.

7. Automated Algorithm for Updating Temperature Distributions

Embodiments for updating the temperature distributions will now be described. An example algorithm is provided below:

1. initialize temperature distributions (initialize mean and variance. Fever distribution higher than normal temp!)
2. Set an isotherm alarm covering all possible human temperatures (including fever)
3. loop
4. if isotherm alarm, capture image and send to SW
5. SW performs face detection
6. if face detected
7. measure temperature
8. if temp above threshold (or perhaps closer to fever distribution)
9. alarm
10. update corresponding distribution (by a controlled learning factor)
11. sleep (time lapse)
12. goto 3.

In various embodiments, the system utilizes existing contrast measure (is a face in focus or not), motion segmentation, visual skin color distributions (if applicable), and/or combine several algorithms/properties to reduce false alarms.

In an effort to reduce/remove static objects located within the scene, a motion segmentation algorithm based on a mixture of Gaussian distributions may be used. In such algorithm, every pixel is modeled as a Gaussian distribution, e.g., with a mean and a variance. If a pixel is close to distribution, (e.g., lies somewhere in between the mean value and the variance) the pixel is said to be background, otherwise it is said to be foreground. This procedure will adapt to the scene and label static objects as background and moving objects as foreground.

In addition, by using an isotherm, only pixels in the wanted temperature range will be considered foreground candidates. By this procedure, the number of false errors in the scene will be reduces even further. After the scene has been segmented into foreground and background (e.g., a binary map with face pixel candidates), the binary map may be cluster size filtered. This may be accomplished by applying a morphological filter (e.g., opening and closing (erosion dilation)). This procedure will filter out small isolated foreground pixels that are considered noise or false positive face pixels. After performing the preceding steps, the remaining foreground pixels are considered to be "face" pixels that may be sent to the face detection algorithm.

8. Elevated Body Temperature Scanning Improvements

In some systems, a measurement box with max temp is used and the alarm threshold is based on a delta from an average temperature of people measured by the system. The average value typically needs to be updated by an operator by manually pressing a button for a certain number of reference persons. To get a good average value, this process may need to be done one every hour on multiple reference persons for crowded area. One problem with this approach is that users don't always reliably perform the process, so the average is fixed with lots of possible false positives and false negatives.

Figure 10A:
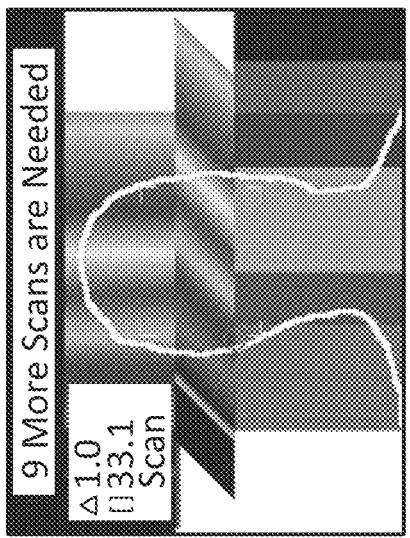
FIG. 10A illustrates an example sampling interface, in accordance with one or more embodiments of the present disclosure.
Figure 10A:
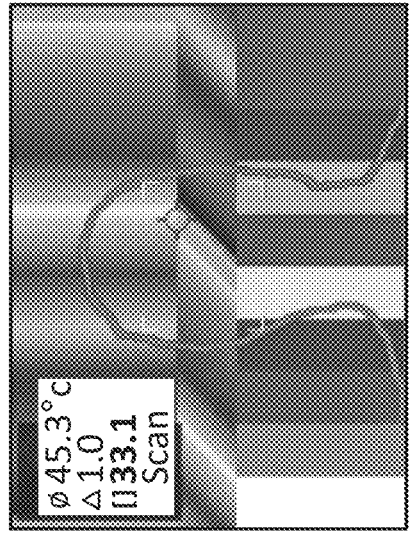
Figure 10A:
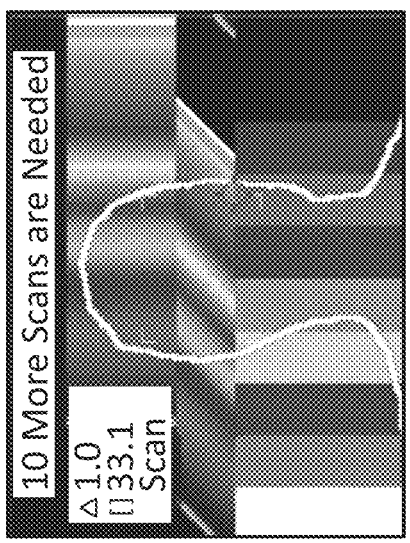
Figure 10A:
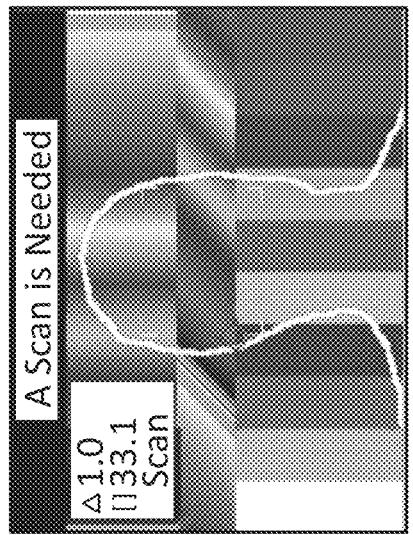
Figure 10A:
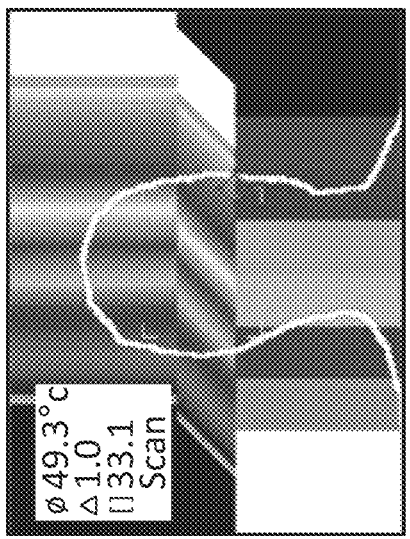

In various embodiment, the average value is updated more often to allow the system to use tighter limits and thus reduce both false positives and false negatives. In one approach, a selfie mode is introduced that flips the image to make it easier for the test subject to correct its position in the image (e.g., aligned with an outline or silhouette on the screen). In another embodiment, GUI support in the screening mode is provided as illustrated in FIG. 10A. As illustrated, when the screening mode is active (as illustrated in image (A)), all irrelevant overlay is removed, and an outline of a head is displayed to help objects/subjects/patients align themselves at a correct distance. Different outlines can be offered as desired to accommodate different types of people, different angles, different distances, etc. In addition, a box that covers the central part of the face is activated. As shown in image (B), the graphics display shows the current average samples, the delta temperature, the current value of the measurement box, and "scan" button to perform a scan.

When enabling screening mode, the user is instructed to take a number of samples (e.g., 10 samples). Samples can be taken by tapping the "scan" button or other selectable item on the screen (e.g., text that says "10 more scans are needed"). As illustrated in image (C) the screen updates to display the number of scans that are remaining. After X minutes the user is reminded to take a new sample, as illustrated in image (D). When the alarm is triggered, as illustrated in image (E), the overlay color is changed (e.g., colored red, flashing/blinking, etc.) to alert the user. A beep or other signal may also be provided.

In other sampling approaches, test subjects press an easily accessible button when they are ready to be measured which updates the average value. Face detection algorithms on visual image flow, thermal image flow, or other flow may be used to detect faces and set measurement boxes in the aligned IR image.

Figure 10B:
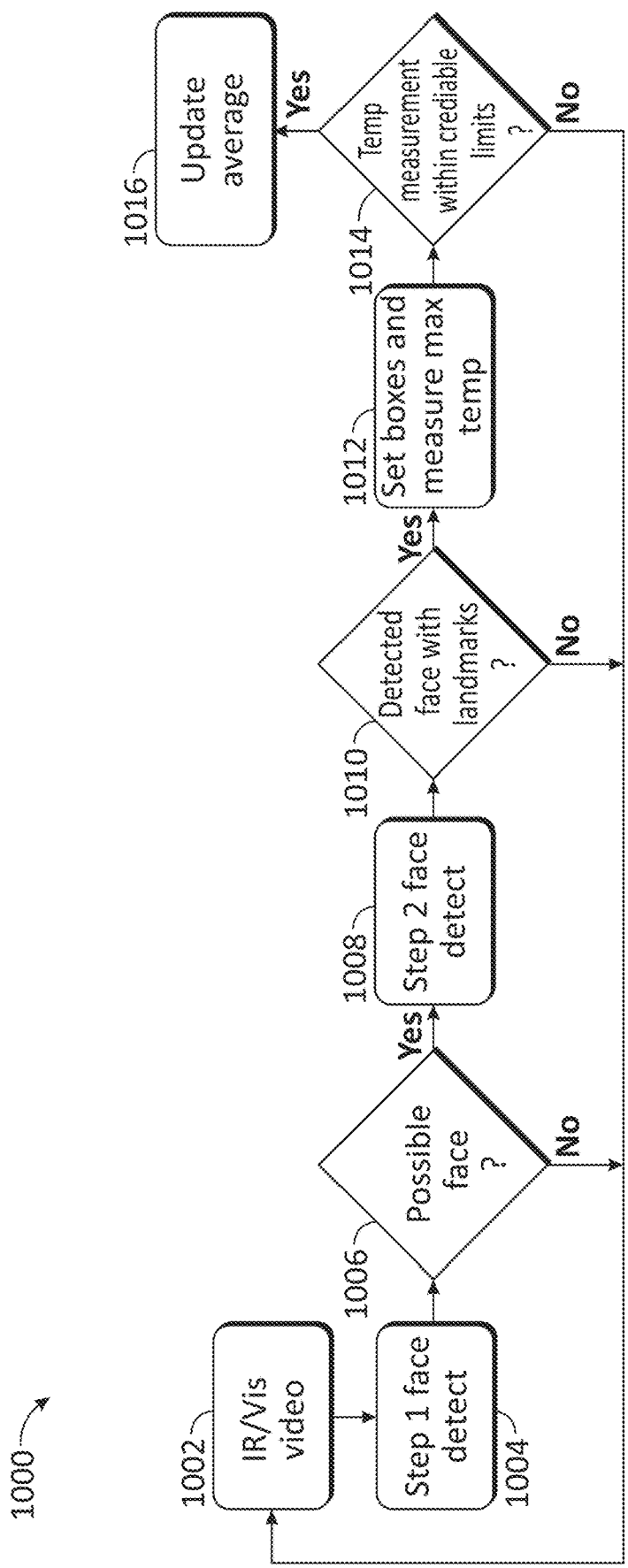
FIG. 10B illustrates an example method for elevated body temperature scanning, in accordance with one or more embodiments of the present disclosure.
Figure 10C:
FIG. 10C illustrates example images using the method of FIG. 10A, in accordance with one or more embodiments of the present disclosure.
Figure 10C:
Figure 10C:
Figure 10C:
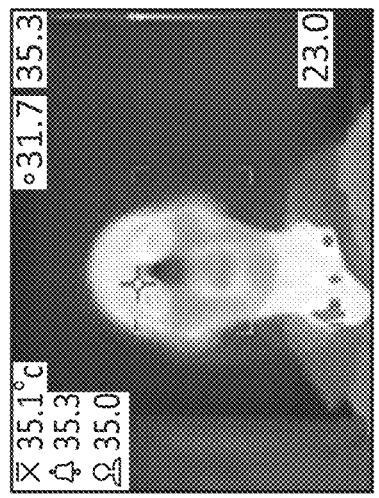
Figure 10C:
Figure 10C:
Figure 10C:
Figure 10C:
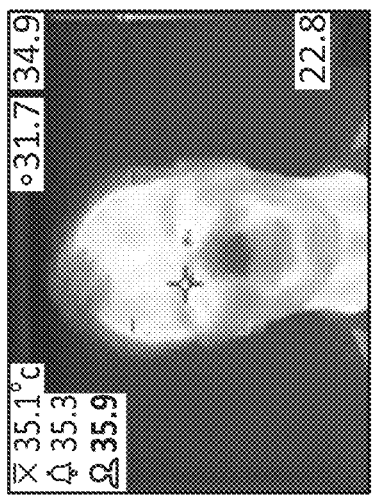
Figure 10C:

Referring to FIGS. 10B and 10C, an example framework and sample images will now be described to train on face detection. In this approach, matching IR and visible images to automatically annotate IR faces from detected faces in visual images, may be used. A process 1000 starts by capturing IR and visible images in step 1002. A face detection algorithm is run on captured visible images in step 1004 and if a possible face is detected (step 1006), a second face detection algorithm is run in step 1008. If a face is detected with discernible landmarks (step 1010), then the system sets boxes and measures the maximum temperature in step 1012. If the temperature measurement if within credible limits for a reference sample (step 1014), then the measurement is used to update the average in step 1016. Sample images using this approach are shown in FIG. 10C.

9. Isotherm Coupled to the Alarm Threshold in EBT

Figure 11:
FIG. 11 illustrates an example method using isotherm coupled to an alarm threshold in an elevated body temperature system, in accordance with one or more embodiments.
Figure 11:

Referring to the images in FIG. 11, an embodiment using isotherm coupled to the alarm threshold in EBT will now be described with reference to one or more embodiments. When the user uses the EBT functionality in the camera, they would typically build up a set of average temperatures and set the camera to alarm when a person has a temperature that is x C higher than the average temperature. This alarm is then displayed as a red flashing value to the left of the image overlay as illustrated in image (A). However, if there is a number of people in the crowd, it can be unclear to the operator who's triggering the alarm, especially if the people are moving.

In some embodiments, an isotherm is applied to the areas that triggers the alarm. Currently, the isotherm requires an absolute temperature threshold which is not appropriate for EBT. In one embodiment, an isotherm of the EBT function is activated and persistent. This could be implemented in the GUI so when the user selects the EBT mode, the user may be able (along with configuring sound etc.) to active the isotherm. Image (B) illustrates an interface for EBT with isotherm on alarm.

10. Temperature Offset to Increase Measurement Accuracy

Some thermal cameras include a feature allowing for temperature offset measurements to measure a surface with a known temperature and use this temperature to adjust radiometry in the image. This feature provides some advantages, including that the measured temperatures have higher accuracy, and less non-uniformity compensation (NUC) processing. By using temperature offset as described, NUC can be disabled which will cause the image quality to slowly degrade, but the radiometric performance will still be acceptable for many applications.

Figures 12A, 12B:
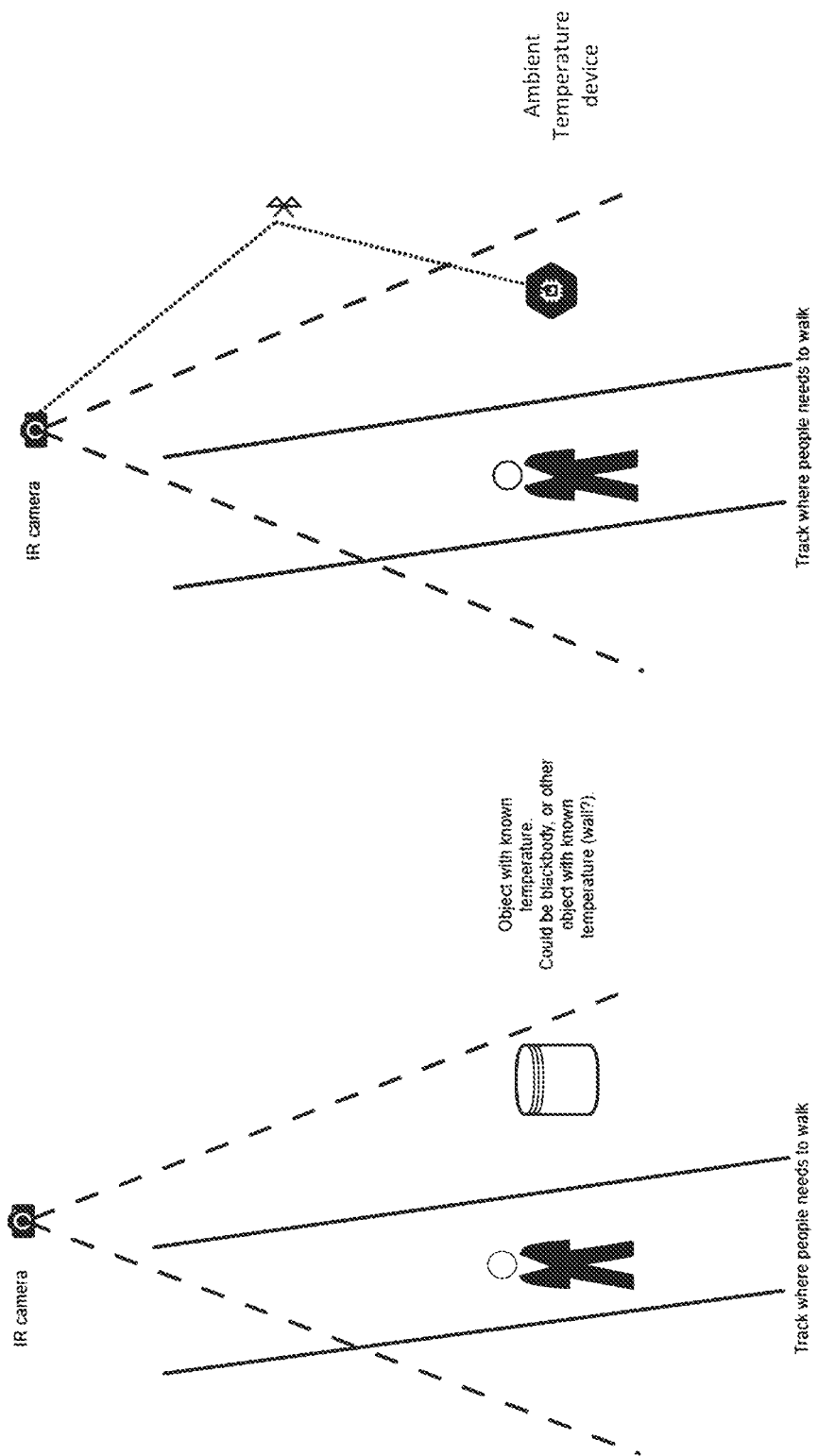
FIGS. 12A and 12B illustrate an example approaches of using temperature offset to increase measurement accuracy, in accordance with one or more embodiments.

In a fever screening scenario using temperature offset could minimize the camera measurement error. In one approach, a fever screening solution performs an average of some people to get a baseline, through a manual process. This average is used to remove camera measurement error and offset that is caused by people coming from a cold (or warm) area (e.g., outside). Using temperature offset could reduce the need for the average in some special circumstances. For example, if the camera is placed inside a building where people are spending a lot of time. This can be used, for example, to monitor the lunch queue to see if someone has developed a fever during the day, monitor walkways in large buildings including hospitals, etc. A setup of this approach is illustrated in FIG. 12A.

Temperature offset may also be adjusted for cases with and without a blackbody. Having a blackbody is may not be ok in many scenarios. An alternative solution would be to use a device that measures the ambient temperature and sends the temperature to the camera. The device has the same temperature as the ambient temperature. A setup of this approach is illustrated in FIG. 12B.

Where applicable, various embodiments provided by the present disclosure can be implemented using hardware, software, or combinations of hardware and software. Also, where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure.

Software in accordance with the present disclosure, such as non-transitory instructions, program code, and/or data, can be stored on one or more non-transitory machine-readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. A method comprising:
   identifying a target in a plurality of infrared images;
   acquiring temperature data associated with the target based, at least in part, on the infrared images, wherein the acquiring comprises sampling temperature data from a measurement location over time and comparing a target temperature trajectory to one or more trajectory models;
   evaluating the temperature data to determine a corresponding temperature classification, wherein the evaluating comprises applying a corresponding trajectory model to the sampled temperature data and applying the model to project a core body temperature;
   processing the identified target in accordance with the temperature classification; and
   detecting a trajectory alarm condition for the sampled temperature data following a corresponding trajectory model.

2. The method of claim 1, wherein the identifying comprises analyzing the infrared images using a convolutional neural network (CNN), the method further comprising:
   training the CNN to identify facial feature points comprising a chin, a mouth, a nose, a left eye, and/or a right eye;
   training the CNN to identify a distance between the target and an image capture device; and
   training the CNN to identify one or more objects in the image comprising a mask, eye glasses, and/or a hat.

3. The method of claim 1, wherein:
   the identifying comprises identifying one or more facial feature points for the target;
   the acquiring comprises identifying a region of interest based on the one or more facial feature points and measuring a temperature of the region of interest using corresponding values from one or more of the infrared images; and
   the evaluating comprises measuring a head pose orientation based on the one or more facial feature points to determine whether the target is in a measurement position.

4. The method of claim 1, wherein:
   the temperature data is associated with the measurement location on the target comprising a cheek, a tear duct, and/or a forehead;
   the evaluating comprises correlating the measurement location with the core body temperature of the target; and
   the method further comprises analyzing a visual image of the target to identify the measurement location.

5. The method of claim 1, further comprising:
   disposing a passive black body in view of a thermal camera configured to capture the infrared images;
   disposing a temperature sensor adjacent to the passive black body;
   sensing a temperature associated with the black body;
   wirelessly transmitting the sensed temperature to the thermal camera; and
   calibrating the thermal camera using the sensed temperature and at least one of the infrared images comprising the passive black body.

6. The method of claim 1, further comprising:
   measuring a temperature of a surface with a known temperature, wherein the surface is a black body, an object with a known temperature, and/or a device that measures ambient temperature; and
   adjusting the temperature data using the measured temperature to account for measurement error.

7. The method of claim 1, further comprising:
   providing a hollow body in view of a thermal camera that captures the infrared images, the hollow body comprising a high emissivity surface at an end facing the thermal camera; and
   processing the image of the high emissivity surface as a black body.

8. The method of claim 1, wherein:
   the acquiring comprises:
      capturing a plurality of visible light images with a visible light camera,
      tracking the target in the visible light images,
      identifying the measurement location on the target, and capturing the infrared images with a thermal camera; and
   the visible light camera has a wider field of view than the thermal camera.

9. The method of claim 8, further comprising:
   instructing the thermal camera to zoom towards the measurement location; and
   wherein the measurement location comprises more pixels in the infrared images than in the visible light images.

10. The method of claim 1, wherein the identifying comprises:
    capturing a plurality of visible light images of a scene;
    detecting a desired measurement location in the visible light images;
    acquiring the infrared images of the desired measurement location;
    analyzing the infrared images to determine a plurality of landmarks within the measurement location;
    selecting one of the landmarks based on a likelihood of accurate temperature measurement;
    establishing a region of interest associated with the selected landmark;
    measuring a maximum temperature within the region of interest; and
    updating reference temperature data for the scene using the measured temperature.

11. The method of claim 1, further comprising: determining a plurality of temperature profiles associated with a plurality of paths for a target within a scene, wherein one or more of the paths extend across multiple scenes captured by a plurality of imaging devices; determining one of the paths associated with the target; and adjusting the temperature data in accordance with the temperature profile for the determined one of the paths.

12. The method of claim 1, further comprising:
acquiring reference temperature samples by rendering a user interface having user prompts configured to guide the user to acquire accurate reference temperature samples;
rendering visual indicia associated with a desired target comprising an outline of a head and/or an alignment box, wherein the visual indicia adapts to a target distance and/or angle; and
rendering an alarm indication if the target is determined to have a fever.

13. A system configured to perform the method of claim 1, the system comprising:
a thermal camera configured to capture the infrared images; and
a logic device configured to perform the identifying, the acquiring, the evaluating, and the processing.

14. The system of claim 13, further comprising:
a passive black body configured to be disposed in view of the thermal camera;
a temperature sensor configured to be disposed adjacent to the passive black body and to sense a temperature associated with the black body;
a wireless interface configured to transmit the sensed temperature to the thermal camera; and
wherein the logic device is configured to calibrate the thermal camera using the sensed temperature and at least one of the infrared images comprising the passive black body.

15. A method comprising:
identifying a target in a plurality of infrared images;
acquiring temperature data associated with the target based, at least in part, on the infrared images;
evaluating the temperature data to determine a corresponding temperature classification;
processing the identified target in accordance with the temperature classification;
selecting a first plurality of measurement locations in one or more captured thermal images;
measuring local contrast of the first measurement locations and excluding measurement locations having a contrast higher than a high contrast threshold, resulting in a second plurality of measurement locations;
measuring a signal at each of the second measurement locations over time;
excluding measurement locations having variation over time over a variation threshold, resulting in a third plurality of measurement locations;
monitoring the signal at each of the third measurement locations; and
using the monitored signal to reduce error in signal measurement due to system drift.

16. A system configured to perform the method of claim 15, the system comprising:
a thermal camera configured to capture the infrared images; and
a logic device configured to perform the identifying, the acquiring, the evaluating, and the processing.

17. A method comprising:
identifying a target in a plurality of infrared images;
acquiring temperature data associated with the target based, at least in part, on the infrared images;
evaluating the temperature data to determine a corresponding temperature classification;
processing the identified target in accordance with the temperature classification;
initializing a temperature distribution associated with a fever;
setting an isotherm alarm covering the temperature distribution;
capturing a thermal image and performing face detection in the thermal image in response to the isotherm alarm;
measuring a temperature of the face; and
updating the temperature distribution if the measured temperature is above a threshold.

18. The method of claim 17, wherein:
the target is a person;
the identifying comprises identifying the person and tracking the person across a subset of the infrared images;
the acquiring comprises identifying a measurement location for the person in the subset of the infrared images and determining the temperature data associated with the location using corresponding values from one or more of the infrared images; and
the evaluating comprises calculating a core body temperature of the person using the temperature data.

19. The method of claim 17, wherein:
the acquiring comprises analyzing thermal data acquired from a measurement location, environmental data associated with a camera location, crowd temperature data associated with a plurality of people associated with the camera location, and/or target temperature data over time using a convolutional neural network (CNN) trained to generate a core body temperature;
the evaluating comprises using a convolutional neural network (CNN) trained to classify the target as one of having a fever or not having a fever; and
the processing comprises generating an alarm condition if the temperature classification indicates the target has a fever.

20. A system configured to perform the method of claim 17, the system comprising:
a thermal camera configured to capture the infrared images; and
a logic device configured to perform the identifying, the acquiring, the evaluating, and the processing.

* * * * *